US012385069B2

(12) United States Patent
Schiller et al.

(10) Patent No.: US 12,385,069 B2
(45) Date of Patent: Aug. 12, 2025

(54) COMPOSITIONS AND METHODS FOR STUDYING THE TAT GENE

(71) Applicant: The Board Of Regents Of The Nevada System Of Higher Education On Behalf Of The University of Nevada, Las Vegas, Las Vegas, NV (US)

(72) Inventors: Martin R. Schiller, Henderson, NV (US); Ronald Benjamin, Henderson, NV (US)

(73) Assignee: The Board Of Regents Of The Nevada System Of Higher Education On Behalf Of The University of Nevada, Las Vegas, NV (US)

( * ) Notice: Subject to any disclaimer, the term of this patent is extended or adjusted under 35 U.S.C. 154(b) by 1869 days.

(21) Appl. No.: 16/318,965

(22) PCT Filed: Jul. 14, 2017

(86) PCT No.: PCT/US2017/042179
§ 371 (c)(1),
(2) Date: Jan. 18, 2019

(87) PCT Pub. No.: WO2018/017419
PCT Pub. Date: Jan. 25, 2018

(65) Prior Publication Data
US 2020/0017883 A1  Jan. 16, 2020

Related U.S. Application Data

(60) Provisional application No. 62/365,537, filed on Jul. 22, 2016.

(51) Int. Cl.
*C40B 20/04* (2006.01)
*C07K 14/005* (2006.01)
*C12N 15/10* (2006.01)
*C12N 15/11* (2006.01)
*C12N 15/113* (2010.01)
*C12N 15/65* (2006.01)
*C12N 15/90* (2006.01)
*C40B 40/08* (2006.01)

(52) U.S. Cl.
CPC .......... *C12N 15/907* (2013.01); *C07K 14/005* (2013.01); *C12N 15/1065* (2013.01); *C12N 15/1086* (2013.01); *C12N 15/111* (2013.01); *C12N 15/113* (2013.01); *C12N 15/65* (2013.01); *C40B 20/04* (2013.01); *C40B 40/08* (2013.01); *C12N 2740/16322* (2013.01); *C12N 2750/14122* (2013.01)

(58) Field of Classification Search
None
See application file for complete search history.

(56) References Cited

U.S. PATENT DOCUMENTS

| | | | | |
|---|---|---|---|---|
| 5,693,508 A | * | 12/1997 | Chang | C07K 14/005 435/456 |
| 2011/0045009 A1 | * | 2/2011 | Nakagawa | A61K 39/385 530/300 |
| 2014/0273226 A1 | | 9/2014 | Wu | |
| 2015/0225730 A1 | * | 8/2015 | Minshull | C12N 15/66 435/91.41 |
| 2015/0344874 A1 | | 12/2015 | Kim et al. | |
| 2015/0359878 A1 | | 12/2015 | Marconi et al. | |
| 2016/0264999 A1 | * | 9/2016 | Rao | C12N 15/907 |
| 2017/0073664 A1 | * | 3/2017 | McCafferty | C12N 9/22 |
| 2017/0247686 A1 | * | 8/2017 | Hamadani | C12N 15/1062 |

OTHER PUBLICATIONS

Aloisio, M. et al., A technical application of quantitative next generation sequencing for chimerism evaluation. Mol Med Rep. 2016; 14(4):2967-74.
Balla, S. et al., Minimotif Miner: a tool for investigating protein function. 2006; Nat Methods. 3(3):175-7.
Banerji, J.L. et al., A Lymphocyte-Specific Cellular Enhancer is Located Downstream of the Joining Region in Immunoglonilin Heavy Chain Genes. Cell. 1983; 33(3):729-40.
Chu, V.T. et al., Increasing the efficiency of homology-directed repair for CRISPR-Cas9-induced precise gene editing in mammalian cells. Nat Biotechnol. 2015; 33:543-8.
Das, A.T. et al., The HIV-1 Tat Protein Has a Versatile Role in Activating Viral Transcription. J Virol. 2011; 85(18):9506-16.
Donahue, D.A. et al., The Viral Protein Tat Can Inhibit the Establishment of HIV-1 Latency. J Virol. 2012; 86:3253-63.
Fiers, W. et al., Complete Nucleotide Sequence of SV40 DNA. Nature. 1978; 273(5658):113-20.
Green, C.B. et al., Construction and real-time RT-PCR validation of Candida albicans PALS-GFP reporter strains and their use in flow cytometry analysis of ALS gene expression in budding and filamenting cells. Microbiol Read Engl. 2005; 151 (pt 4):1051-60.
Greenaway, P.J. et al., Human Cytomegaovirus DNA: BamHI, EcoRI and PstI Restriction Endonuclease Cleavage Maps. Gene. 1982; 18(3):355-60.
Gurtu, V. et al., IRES bicistronic expression vectors for efficient creation of stable mammalian cell lines. Biochem Biophys Res Commun. 1996; 229(1):295-8.
Jiang, T. et al., Recent developments of biological reporter technology for detecting gene expression. Biotechnol Genet Eng Rev. 2008; 25(1):41-76.

(Continued)

*Primary Examiner* — Maria Marvich
(74) *Attorney, Agent, or Firm* — BALLARD SPAHR LLP

(57) ABSTRACT

Disclosed are compositions and methods for studying a Tat gene. Specifically, the disclosure provides a vector comprising a double-stranded nucleic acid construct which comprises a Tat gene and a green fluorescent protein (GFP) reporter element, and further wherein the double-stranded nucleic acid construct comprising AAVS1 (adeno-associated virus integration site, a safe harbor locus) arms that flank on both sides of the Tat gene and the reporter element for integration at the human AAVS1 site by homologus recombination. Further provided are methods of using a cell comprising the vector for studying the effects of exogenous conditions on expression of the Tat gene.

1 Claim, 13 Drawing Sheets

(56) References Cited

OTHER PUBLICATIONS

Kain, S.R. et al., Green fluorescent protein as a reporter of gene expression and protein localization. BioTechniques. 1995; 19(4):650-65.

Laimins, L.A. et al., Osmotic Control of kdp Operon Expression in *Escherichia coli*. Proc Natl Acad Sci USA. 1981; 78(1):464-8.

Lusky, M.L. et al., Bovine Papilloma Virus Contains an Activator of Gene Expression at the Distal End of the Eatly Transcription Unit. Mol Cell Biol. 1983; 3(6):1108-22.

Maggio et al., Adenoviral Vector Delivery of RNA-Guided CRISPR/CAS9 Nuclease Complexes Induces Targeted Mutagenesis in a Diverse Array of Human Cells. Sci Reports. 2014; 4:5105 (11 pages).

Mann, M.J., and Dzau, V.J., Therapeutic applications of transcription factor decoy oligonucleotides. J Clin Invest. 2000; 106(9):1071-5.

Mishin, A.S. et al., Novel Uses of Fluorescent Proteins. Curr Opin Chem Biol. 2015; 27:1-9.

Müther et al., Viral Hybrid Vectors for Somatic Integration—Are They the Better Solution? Viruses. 2009; 1(3):1295-324.

Oceguera-Yanez et al., engineering the AAVS1 Locus for Consistent and Scalable Transgene Expression in Human iPSCs and Their Differentiated Derivatives. Methods. 2016; 101:43-55.

Osborne, T.F. et al., Transcription Control Region with the Protein-Coding Portion of Adenovirus E1A Genes. Mol Cell Biol. 1984; 4(7):1293-305.

Palmer, A.E. et al., Design and Application of Genetically Encoded Biosensors. Trends Biotechnol. 2011; 29(3):144-52.

Pearson, W.R., Rapid and sensitive sequence comparison with FASTP and FASTA. Methods Enzymol. 1990; 183:63-98.

Puntervoll, P. et al., ELM server: A new resource for investigating short functional sites in modular eukaryotic proteins. Nucleic Acids Res. 2003; 31(13):3625-30.

Rogers, J.K. and Church, G.M., Genetically Encoded Sensors Enable Real-Time Observation of Metabolite Production. Proc Natl Acad Sci USA. 2016; 113(9):2388-93.

Stornaiuolo et al., RD2-MolPack-Chim3, a Packaging Cell Line for Stable Production of Lentiviral Vectors for Anti-HIV Gene Therapy. Hum Gene Ther Meth. 2013; 24(4):228-40.

Ujihira, T., et al., MicroRNA-574-3p, identified by microRNA library-based functional screening, modulates tamoxifen response in breast cancer. Sci Rep. 2015; 5:7641 (9 pages).

Vyas, J. et al., A proposed syntax for Minimotif Semantics, version 1. BMC Genomics. 2009; 10(1):360 (13 pages).

\* cited by examiner

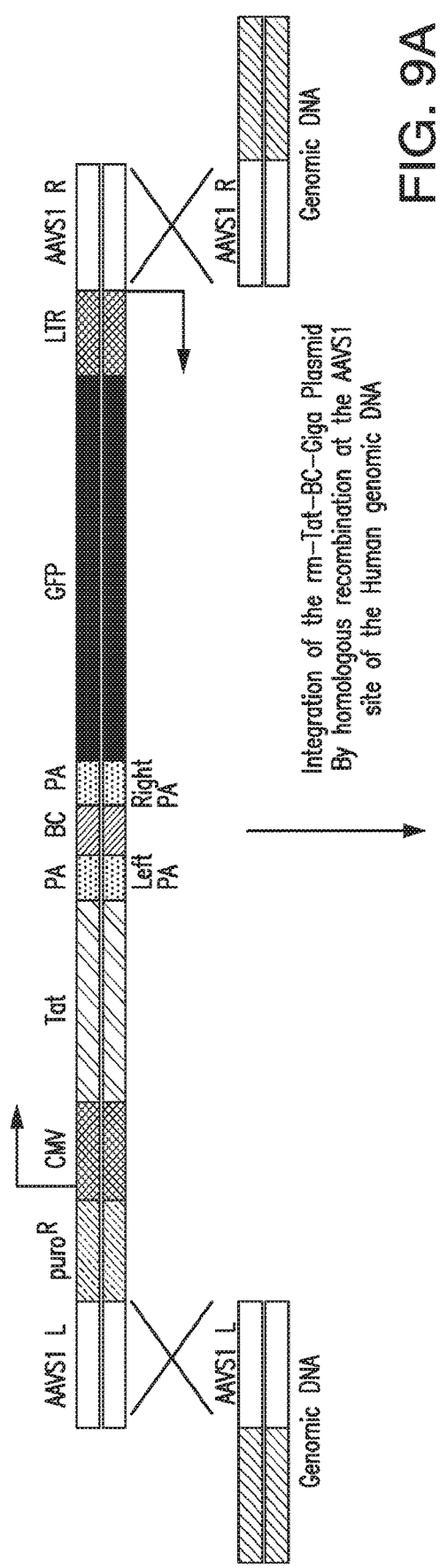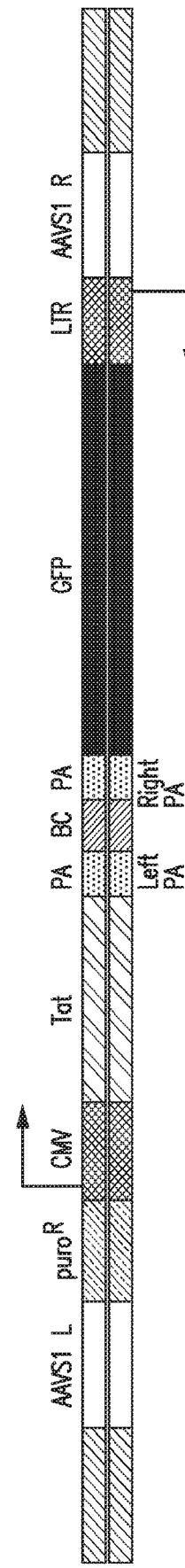

COMPOSITIONS AND METHODS FOR STUDYING THE TAT GENE

CROSS REFERENCE TO RELATED APPLICATIONS

This application claims the benefit of priority under U.S.C. § of International Application No. PCT/US2017/042179 filed on Jul. 14, 2017 which claims priority to U.S. Provisional Application No. 62/365,537 filed on Jul. 22, 2016. The content of these earlier filed applications are hereby incorporated by reference in its entirety.

STATEMENT REGARDING FEDERALLY FUNDED RESEARCH

This invention was made with government support under grant numbers GM10789 and AI116411 awarded by National Institutes of Health. The government has certain rights in the invention.

BACKGROUND

Biomedical research is currently limited, at least in part, because relatively few high throughput assays are available. The high throughput assays, that are available, however, are limited to assessing a confined number of questions. For example, RNASeq and MicroArrays can be used to identify RNAs and assess their presence and level of expression in the transcriptomes, but are limited to transcript identify and expression levels. Furthermore, the few high throughput assays that assess molecular or cellular function are limited to a few specialized applications. Thus, compositions and methods that can be used to evaluate at an expanded level of detail, multiple (e.g. thousands, millions or even billions) single cells in a single high throughput assay is needed.

BRIEF DESCRIPTION OF THE DRAWINGS

FIG. 1 shows an example of a disclosed vector and an example of a method of using said vector.

FIG. 3 also shows one method of determining the effect of a driver element on a reporter element as described herein.

FIG. 4A shows the fluorescence microscopy imaging of LentiX293T cells with four categories of vectors independently transfected sets: (i) Giga noTat/LTR-GFP (ii) Giga-wt Tat/LTR-GFP, (iii) Giga-mTat1/LTR-GFP and (iv) Giga-mTat2/LTR-GFP. FIG. 4B shows the results of real time PCR analyses showing that wild-type (wt)-Tat (driver element) transactivates the LTR/GFP (reporter element) to express 10-fold GFP transcripts relative to mTat1 and 100 fold relative to mTat2 from a cDNA pool mix prepared from the RNA isolated from LentiX293T cells transfected with Giga-wtTat/LTR-GFP, Giga-mTat1/LTR-GFP and Giga-mTat2/LTR-GFP.

FIG. 7A shows that the double-stranded nucleic acid construct consists of AAVS1 L and AAVS1 R arms that flank either side of the GigaAssay cassette. FIG. 7B shows the double-strand break mediated by gRNA-Cas-9 at AAVS1 site and permits the GigaAssay cassette to integrate at the human AAVS1 site by homologus recombination.

FIGS. 9A-B shows an exemplary method of using a vector comprising a double-stranded nucleic acid construct comprising a Tat gene and a GFP reporter element and the design thereof. FIG. 9A shows that the double-stranded nucleic acid construct consists of AAVS1 L and AAVS1 R arms that flank either side of the GigaAssay cassette. FIG. 9B shows the double-strand break mediated by gRNA-Cas-9 at AAVS1 site and permits the GigaAssay cassette to integrate at the human AAVS1 site by homologus recombination.

SUMMARY

Figure 1A:
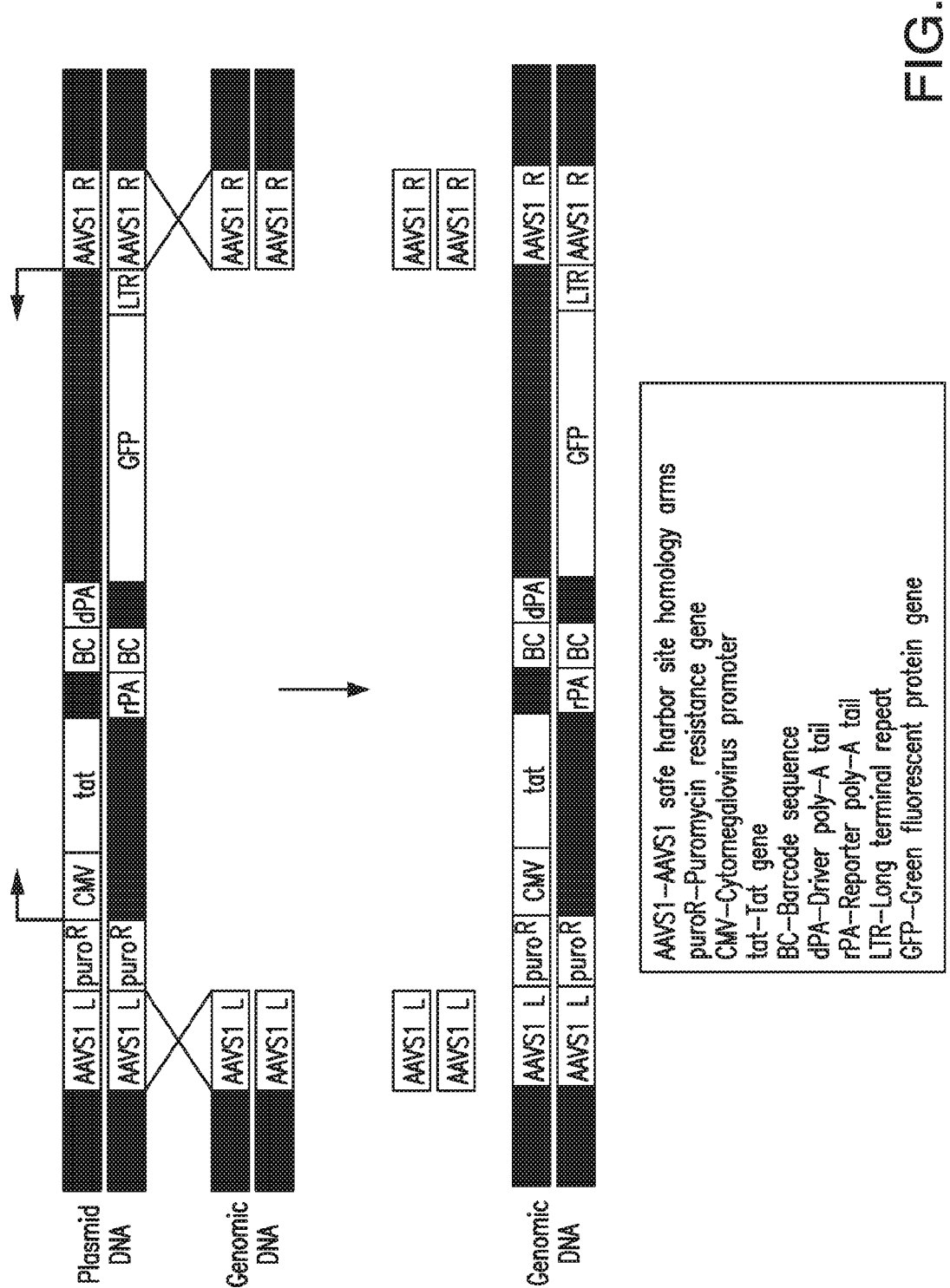
FIG. 1A is a schematic of the disclosed vector.

The GigaAssay is an ultra high throughput system where up to a billion mammalian cells and replicates are each individually assayed for multiple aspects of molecular structure and/or function using flow sorting and next generation sequencing. An experiment on a single culture assesses millions of instances of a variable such as different point mutants, overexpressed genes, silenced genes, gene knockouts, or any combinations thereof.

The GigaAssay described herein can be used to study any organism including but not limited to an animal, plant or a single-celled life form (e.g., bacterium). The organism can be a prokaryote or a eukaryote. The GigaAssay described herein can also be used to study viruses.

The GigaAssay, vectors and constructs described herein can be used to improve or study the function of any component of the vectors or constructs disclosed herein. For example, the GigaAssay, vectors and constructs described herein can be used to study or understand the effect of a driver element, a reporter element, a library of driver elements, a library of reporter elements, a promoter operably linked to a driver element or driver element library, a promoter operably linked to a reporter element or reporter element library, a GADEL, a GAREL, a library of promoters operably linked to a driver element or driver element library, a library of promoters operably linked to a reporter element or reporter element library, or a selectable marker.

In some aspects, exogenous conditions can be applied to a cell comprising a double-stranded nucleic acid construct as disclosed herein in order to determine the effect of the exogenous condition on a driver element, a reporter element, a library of driver elements, a library of reporter elements, a promoter operably linked to a driver element or driver element library, a promoter operably linked to a reporter element or reporter element library, a GADEL, a GAREL, a library of promoters operably linked to a driver element or driver element library, a library of promoters operably linked to a reporter element or reporter element library, or a selectable marker. Exogenous conditions can include any environmental factor (e.g. pH, heat, light, cellular stress), a potential therapeutic agent (e.g. an antibody, small molecule, therapeutic peptide), or any other agent that may affect one or more of the components of the disclosed vectors or constructs.

In some aspects, the endogenous environment of a cell comprising a double-stranded nucleic acid construct as disclosed herein can be analyzed in order to determine the effect of the endogenous environment of the cell on a driver element, a reporter element, a library of driver elements, a library of reporter elements, a promoter operably linked to a driver element or driver element library, a promoter operably linked to a reporter element or reporter element library, a GADEL, a GAREL, a library of promoters operably linked to a driver element or driver element library, a library of promoters operably linked to a reporter element or reporter element library, or a selectable marker. Exogenous conditions can include any environmental factor (e.g. pH, heat, light, cellular stress), a potential therapeutic agent (e.g. an antibody, small molecule, therapeutic peptide), or any other agent that may affect one or more of the components of the disclosed vectors or constructs.

As provided herein, in an aspect, the GigaAssay can be used recursively.

Disclosed herein are vectors comprising double-stranded nucleic acid constructs, wherein the double-stranded nucleic acid constructs comprises a first strand and a second strand, wherein the first strand comprises from 5' to 3' a 5' ARM sequence, a GADE sequence and a 3' ARM sequence; wherein the second strand comprises from 5' to 3' a 3' ARM sequence, a GARE sequence and a 5' ARM sequence; and wherein the first strand is complementary to the second strand.

Disclosed herein are vectors comprising double-stranded nucleic acid constructs, wherein the double-stranded nucleic acid constructs comprise a first strand a second strand, wherein the first strand comprises from 5' to 3', an AAVS1 locus sequence; a nucleic acid sequence complementary to puromycin N-acetyl-transferase; a CMV promoter; a tat cDNA coding sequence; a 3' UTR, wherein the 3' UTR comprises a barcode sequence, and a poly(A) signal; a sequence complementary to a GFP sequence, a sequence complementary to an LTR; a sequence complementary to an AAVS1 locus sequence of the second strand; and a functional sequence; wherein the second strand comprises from 5' to 3', an AAVS1 locus sequence; a LTR promoter; a GFP sequence; a 3' UTR, wherein the 3' UTR comprises a sequence complementary to the poly(A) sequence of the 3' UTR of the first strand, a barcode sequence complementary to the barcode sequence of the barcode sequence of the first strand, and a SV40 nuclear localization signal; a sequence complementary to the tat sequence and the CMV promoter of the first strand; a sequence encoding puromycin N-acetyl-transferase; a sequence complementary to an AAVS1 locus sequence of the first strand; and a functional sequence.

Disclosed herein are vectors comprising double-stranded nucleic acid constructs, wherein the double-stranded nucleic acid constructs comprise a first strand a second strand, wherein the first strand comprises from 5' to 3', an AAVS1 locus sequence; a nucleic acid sequence complementary to puromycin N-acetyl-transferase; a CMV promoter; a tat cDNA coding sequence; a 3' UTR, wherein the 3' UTR comprises a nucleic acid sequence complementary to a synthetic poly(A) signal of the 3'UTR of the second strand, a barcode sequence complementary to the barcode sequence of the second strand, and a polySV40(A) signal; a sequence complementary to a GFP sequence, a sequence complementary to an LTR; a sequence complementary to an AAVS1 locus sequence of the second strand; and a functional sequence; wherein the second strand comprises from 5' to 3', an AAVS1 locus sequence; a LTR promoter; a GFP sequence; a 3' UTR, wherein the 3' UTR comprises a sequence complementary to the polySV40(A) sequence of the 3' UTR of the first strand, a barcode sequence complementary to the barcode sequence of the barcode sequence of the first strand, and a synthetic poly(A) signal; a sequence complementary to the tat sequence and the CMV promoter of the first strand; a sequence encoding puromycin N-acetyl-transferase; a sequence complementary to an AAVS1 locus sequence of the first strand; and a functional sequence.

DETAILED DESCRIPTION

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "comprising" can include the aspects "consisting of" and "consisting essentially of."

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

"Inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels.

"Modulate", "modulating" and "modulation" as used herein mean a change in activity or function or number. The change may be an increase or a decrease, an enhancement or an inhibition of the activity, function, or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100 percent, or more, or any amount of promotion in between compared to native or control levels. In an aspect, the increase or promotion is 10-20, 20-30, 30-40, 40-50, 50-60, 60-70, 70-80, 80-90, or 90-100 percent as compared to native or control levels. In an aspect, the increase or promotion is 0-25, 25-50, 50-75, or 75-100 percent, or more, such as 200, 300, 500, or 1000 percent more as compared to native or control levels. In an aspect, the increase or promotion can be greater than 100 percent as compared to native or control levels, such as 100, 150, 200, 250, 300, 350, 400, 450, 500 percent or more as compared to the native or control levels.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

"Homology" refers to two nucleic acid or protein sequences that have more sequence similarity or identity than would be observed by random chance inferring that the organism sources of the sequences have a common ancestry or have descending from common evolutionary ancestor.

"Identity" is the percentage of characters that match exactly between two different protein or nucleic acid sequences. Hereby, gaps are not counted and the measurement is relational to the shorter of the two sequences.

Sequence "similarity" is a measure of an empirical relationship between two protein or nucleic acid sequences.

The term "contacting" as used herein refers to bringing a compound or test agent and a cell, target receptor, or other biological entity together in such a manner that the compound or test compound can affect the activity of the target (e.g., receptor, transcription factor, cell, etc.), either directly; i.e., by interacting with the target itself.

As used herein, the term "level" refers to the amount of a target molecule in a sample, e.g., a sample from a subject. The amount of the molecule can be determined by any method known in the art and will depend in part on the nature of the molecule (i.e., gene, mRNA, cDNA, protein, enzyme, etc.). The art is familiar with quantification methods for nucleotides (e.g., genes, cDNA, mRNA, etc.) as well as proteins, polypeptides, enzymes, etc. It is understood that the amount or level of a molecule in a sample need not be determined in absolute terms, but can be determined in relative terms (e.g., when compares to a control (i.e., a non-affected or healthy subject or a sample from a non-affected or healthy subject) or a sham or an untreated sample).

The phrase "at least" preceding a series of elements is to be understood to refer to every element in the series. For example, "at least one" includes one, two, three, four or more.

As used herein, the term "sequence of interest" is the object of sequencing and can be any nucleic acid. As used herein, the term "sequence of interest" can refer to a portion of a "target nucleic acid molecule," "target sequence," "target nucleic acid," or "target polynucleotide" and the like. The sequence of interest can include multiple nucleic acid molecules, multiple sites in a nucleic acid molecule, or a single region of a nucleic acid molecule. A sequence of interest can be in any nucleic acid sample of interest and of any length. The term "sequence of interest" can also mean a nucleic acid sequence (e.g., a gene), that is partly or entirely heterologous, i.e., foreign, to a cell into which it is introduced. The term "sequence of interest" can also mean a nucleic acid sequence that is partly or entirely homologous to an endogenous gene of the cell into which it is introduced. For example, a sequence of interest can be cDNA, DNA, or RNA including mRNA and rRNA or others. The term "sequence of interest" can also mean a nucleic acid sequence that is partly or entirely complementary to an endogenous gene of the cell into which it is introduced.

The term "vector" or "construct" refers to a nucleic acid sequence capable of transporting into a cell another nucleic acid where it can be replicated and/or expressed. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. As disclosed herein, the term "vector", "plasmid" or "construct" can comprise one or more of the double-stranded nucleic acid constructs disclosed herein The term "transfection" refers to the introduction of a nucleic acid, (e.g., an expression vector) into a recipient cell including introduction of a nucleic acid to the chromosomal DNA of said cell.

As used herein, "transformation" refers to the genetic alteration of a cell that occurs by the uptake or incorporation of exogenous genetic material from its surroundings (e.g., cell membrane(s)).

As used herein, the term "GigaAssay" refers to a single cell assay that can independently measure something (e.g., to identify which indels effect a particular gene function) in multiple (e.g., billions) of cells at the same time.

As used herein, the term "GADEL" refers to "GigaAssay Driver Element Library," a collection of DNA, RNAs, or proteins encoded by DNA that can be tested for their effects in a molecular cell-based assay. Each clone can be inserted in a single cell.

As used herein, the term "GAREL" refers to "GigaAssay Reporter Element Library," a collection of DNA, RNAs, or proteins encoded by the DNA that can serve as a sequence-based and/or biophysical readout for GADELs in a molecular cell-based assay. Each clone can be inserted in a single cell.

As used herein, the term "GADE" or "GADE sequence" refers to a portion of the double-stranded nucleic acid constructs disclosed herein that comprises a transcriptional control element operably linked to one or more driver elements and a 3'UTR. The 3'UTR of a GADE comprises a barcode sequence. The barcode sequence of the GADE is complementary to a barcode sequence in the 3'UTR of a GARE present on the opposite strand of the double-stranded nucleic acid construct.

As used herein, the term "GARE" or "GARE sequence" refers to a portion of the double-stranded nucleic acid constructs disclosed herein that comprises a transcriptional control element operably linked to one or more reporter elements and a 3'UTR. The 3'UTR of the GARE comprises a barcode sequence. The barcode sequence of the GARE is complementary to a barcode sequence in the 3'UTR of a GADE present on the opposite strand of the double-stranded nucleic acid construct.

As used herein, the phrase "GigaAssay cassette" refers to a double-stranded DNA construct comprising a GADE sequence, a GARE sequence, a barcode sequence, a selectable marker, and two ARMS (e.g., a 3' ARM and a 5' ARM) for insertion into an insertion site of a target locus (e.g. a safe harbor locus), wherein the two ARMS flank the selectable marker/GADE sequence and GARE sequence. Further, the 3' ARM and 5' ARM target adjacent regions of the locus flanking the insertion site. An insertion site of a target locus can be any site within a cellular genome that is substantially identical to the 3' ARM and 5' ARM sequences. The insertion site can be flanked by an exogenously added or engineered sequence. For example, an insertion site can utilize Cre/loxP technology where the Cre recombinase will excise any region of DNA placed between two loxP sites (locus of X-ing over) (Sauer and Henderson, 1998; Sternberg and Hamilton, 1981). Another example includes the use of the Flp recombinase that can be used to provide a similar means to rearrange a genetic locus. Flp (flippase) was isolated from *Saccharomyces cervisiae* and, like Cre, the recombinase will also excise DNA flanked between 34 bp sequences known, in this case, as FRT sites (Dymecki, 1996). In addition to spatial excision of a floxed allele, temporal control of Cre-mediated recombination is also possible.

As used herein, the phrase "cell group" or "clonal cell group" refers to a set of cells originating from a cell comprising a GigaAssay cassette.

Disclosed herein is the GigaAssay, a high throughput assay technology that permits the analysis of millions of gene/s or mutants or any functionally classified set of sequences for a biological function at an unprecedented level of detail and speed. The GigaAssay is an ultra-high throughput assay system that can be used to run an assay on up to billions single cells each with up to six variable or libraries at the same time using RNAseq, other NGS analyses or a reporter as the readout. The system is implemented by transfection, transduction, or other means of introducing a plasmid or viral vector comprising one or more of the disclosed double-stranded nucleic acid constructs or GigaAssay cassettes into a cell or organism population, optionally treating or sorting the cells or organisms, performing RNAseq, and analyzing the results. Described herein is the testing of the transcriptional activity of over 1 million HIV Tat mutants tested with a LTR-GFP reporter. Although this is one of the best studied genes, testing of less than 400 mutants is reported in the scientific literature. This technology can be used to explore a multitude of biological systems at an unprecedented level of detail and speed, thus permitting investigation of complex systems, resulting in the answers to biological questions that could not previously be tested.

In some aspects, the approach to the GigaAssay is to first generate a heteroallelic cell line such that one GigaAssay cassette can be integrated into a single locus of each individual cell. If, for example, a cell were diploid or of higher ploidy, the possibility of integration of more than one GigaAssay cassette could confound the experimental interpretation.

Next, a vector that encodes a GigaAssay cassette can be created (e.g. as shown in FIG. 1A). In some aspects, the vector can be transfected, infected, transformed, or transduced into a large population of cells. In some aspects, the cells can be from any kingdom or source. In some aspects, transfected, infected or transduced cells can be selected based on, for example, the presence of identification of a selectable marker within the cassette. In some aspects, the transfected, infected or transduced cell can contain an integrated library clone comprising one or more DNA barcodes.

The cells described herein can proliferate, resulting in more than one (e.g., multiple copies) of each cell, thus forming a clonal cell group. The clonal cell group can be more than one cell (e.g, at least two cells) comprising the GigaAssay cassette that further comprises the same barcode. These cells can then be chemically or physically treated as desired based on the question of interest. For example, if a fluorescent reporter is present in the cassette (e.g., GigaAssay cassette), the cells can be flow sorted to select the cells to be used.

Figure 1B:
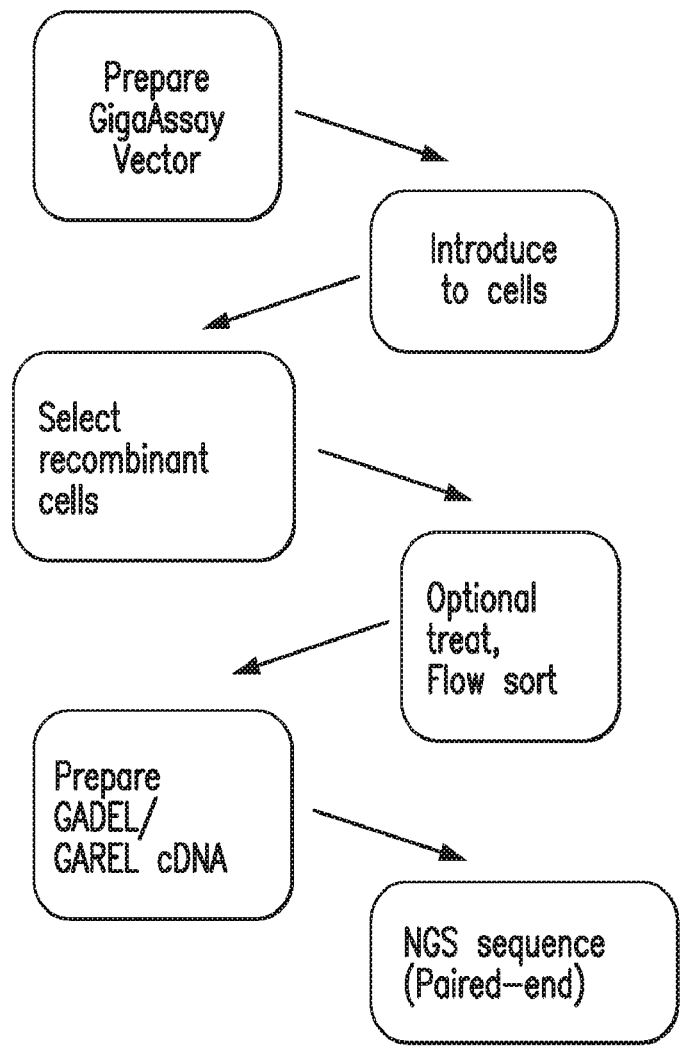
FIG. 1B is an example of the method disclosed herein using the vector described herein.

In some aspects, the RNA, and optionally genomic DNA can be extracted and cDNA can be made for the two transcripts expressed in each cell, e.g., the driver and reporter (see e.g. FIG. 1B). In an aspect, these transcripts can be used to match or identify a clonal cell group by using a barcode (described herein). In an aspect, these transcripts can be used to match (or identify) an RNA to a genomic DNA by using a barcode. Next, RNA, and optionally genomic DNA, can be extracted. cDNA can be made for the two transcripts expressed in each cell, referred to as the driver and the reporter. These transcripts can be matched as coming from the same clonal cell group later using the barcode wherein the barcode on one of transcripts can be the reverse complement for the barcode on the other type of transcript coming from the same cell. In some aspects, the RNA, and optionally DNA can be further analyzed, for example, by sequencing by Next Generation Sequencing (NGS) to determine the identity and read number of transcripts with each barcode. The NGS data can be analyzed to provide a quantitative assay assessing, for example, millions (Aloisio et al., 2016), even billions, of instances of the variable encoded in the vector. For example, the variable can be one or more libraries of cDNAs, siRNAs, mutants or genetic variants, reporters, gDNA fragments, UTRs, or promoters.

Disclosed herein are vectors or cassettes (sometimes referred to as GigaAssay vectors or GigaAssay cassettes or double-stranded nucleic acid constructs) comprising a GigaAssay driver element library, GigaAssay reporter element library, two homologous arms and optionally a selectable marker. As disclosed herein, the GigaAssay reporter element library comprises a barcode. As disclosed herein, the GARE sequences and GADE sequences can comprise one or more barcode sequences. In an aspect, the two ARMS can be identical, substantially identical to, or homologous with the desired insertion site in the genome.

Disclosed herein are double-stranded nucleic acid constructs. In an aspect, the double-stranded nucleic acid constructs can be DNA. In an aspect, the double-stranded nucleic acid constructs can comprise a first strand and a second strand.

Disclosed herein are vectors comprising double-stranded nucleic acid constructs. The double-stranded nucleic acid constructs can comprise a first strand and a second strand. In some aspects, the first strand can comprise from 5' to 3', a 5' ARM sequence, a GADE sequence and a 3' ARM sequence. In some aspects, the second strand can comprise from 5' to 3', a 3' ARM sequence, a GARE sequence and a 5' ARM sequence. The first strand can be complementary to the second strand and preferably can be complementary to the second strand.

In an aspect, the vector can be a viral vector. In an aspect, the viral vector can be self-inactivating.

In an aspect, the vector can comprise a double-stranded nucleic acid construct. The double-stranded nucleic acid construct can comprise a first strand a second strand. In an aspect, the first strand can comprise from 5' to 3', an AAVS1 locus sequence; a nucleic acid sequence complementary to puromycin N-acetyl-transferase; a CMV promoter; a tat cDNA coding sequence; a 3' UTR, wherein the 3' UTR comprises nucleic acid sequence complementary to a synthetic poly(A) signal of the 3'UTR of the second strand, a barcode sequence complementary to the barcode sequence of the second strand, and a polySV40(A) signal; a sequence complementary to a GFP sequence, a sequence complementary to an LTR; a sequence complementary to an AAVS1 locus sequence of the second strand; and a functional sequence. In an aspect, the second strand can comprise from 5' to 3', an AAVS1 locus sequence; a LTR promoter; a GFP sequence; a 3' UTR, wherein the 3' UTR comprises a sequence complementary to the polySV40(A) sequence of the 3' UTR of the first strand, a barcode sequence complementary to the barcode sequence of the barcode sequence of the first strand, and a synthetic poly(A) signal; a sequence complementary to the tat sequence and the CMV promoter of the first strand; a sequence encoding puromycin N-acetyl-transferase; a sequence complementary to an AAVS1 locus sequence of the first strand; and a functional sequence.

Disclosed herein are transcriptional control elements (TCEs). TCEs are elements capable of driving expression of nucleic acid sequences operably linked to them. The constructs disclosed herein comprise at least one TCE. TCEs can optionally be constitutive or regulatable.

Also disclosed are constructs disclosed herein comprising first and second transcriptional control elements oriented in opposite directions wherein the activity of one of the transcriptional control elements can affect the activity of the other transcriptional control elements. Optionally, the two transcriptional control elements can be juxtaposed or a linker sequence can be located between the first and second transcriptional control elements.

The presence of a regulatable TCE and a regulator sequence, whether they are on the same or a different construct, allows for inducible and reversible expression of the sequences operably linked to the regulatable TCE. As such, the regulatable TCE can provide a means for selectively inducing and reversing the expression of a sequence of interest.

Regulatable TCEs can be regulatable by, for example, tetracycline or doxycycline. Furthermore, the TCEs can optionally comprise at least one tet operator sequence. In one example, at least one tet operator sequence can be operably linked to a TATA box.

Furthermore, the TCE can be a promoter, as described elsewhere herein. Examples of promoters useful with the packaging constructs disclosed herein are given throughout the specification. For example, promoters can include, but are not limited to, CMV based, CAG, SV40 based, heat shock protein, a mH1, a hH1, chicken β-actin, U6, Ubiquitin C, or EF-1α promoters.

Additionally, the TCEs disclosed herein can comprise one or more promoters operably linked to one another, portions of promoters, or portions of promoters operably linked to each other. For example, a transcriptional control element can include, but are not limited to a 3' portion of a CMV promoter, a 5' portion of a CMV promoter, a portion of the βactin promoter, or a 3'CMV promoter operably linked to a CAG promoter.

In some aspects, promoters controlling transcription from vectors in mammalian host cells can be obtained from various sources, for example, the genomes of viruses such as polyoma, Simian Virus 40 (SV40), adenovirus, retroviruses, hepatitis B virus and most preferably cytomegalovirus, or from heterologous mammalian promoters, e.g., β-actin promoter. The early and late promoters of the SV40 virus are conveniently obtained as an SV40 restriction fragment, which also contains the SV40 viral origin of replication (Fiers et al., Nature, 273: 113 (1978) which is incorporated by reference herein in its entirety for viral promoters). The immediate early promoter of the human cytomegalovirus is conveniently obtained as a HindIII E restriction fragment (Greenway, P. J. et al., Gene 18: 355 360 (1982) which is incorporated by reference herein in its entirety for viral promoters). Of course, promoters from the host cell or related species also are useful herein, and can be used for tissue specific gene expression or tissues specific regulated gene expression. The cited references are incorporated herein by reference in their entirety for their teachings of promoters.

"Enhancer" generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Each of the cited references is incorporated herein by reference in their entirety for their teachings of enhancers. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). Each of the cited references is incorporated herein by reference in their entirety for their teachings of potential locations of enhancers. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin (bp 100 270), the cytomegalovirus early promoter enhancer, the polyoma enhancer on the late side of the replication origin, and adenovirus enhancers.

"Insulator" generally refers to nucleic acid sequences that serve to insulate the expression of a given gene in a cellular system. An insulator can allow expression of a driver or reporter element even if the driver or reporter element is integrated into heterochromatin of a cell. As described herein, an insulator can be a chromosomal insulator. A chromosomal insulator can reduce the interference between two promoters. For example, a chromosomal insulator can reduce the interference between two promoters contained in the constructs disclosed herein, thereby reducing leakage of one of the promoters.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region are active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression of nucleic acid sequences operably linked to the transcriptional control elements in the gene transfer constructs described herein can also be regulated by Cre recombinase.

As used herein, the terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription.

Suitable promoters can be derived from genes of the host cells where expression should occur or from pathogens for this host cells (e.g., tissue promoters or pathogens like viruses). If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence or gene of interest to a specific type of tissue in the relative absence of expression of the same nucleotide sequence or gene of interest in a different type of tissue.

Also disclosed are Internal Ribosome Entry Sites (IRES) and Internal Ribosome Entry Site-Like elements. Internal Ribosome Entry Sites (IRES) are cis-acting RNA sequences able to mediate internal entry of the 40S ribosomal subunit on some eukaryotic and viral messenger RNAs upstream of a translation initiation codon. Although sequences of IRESs are diverse and are present in a growing list of mRNAs, IRES elements contain a conserved Yn-Xm-AUG unit (Y, pyrimidine; X, nucleotide), which appears essential for IRES function. Novel IRES sequences continue to be added to public databases every year and the list of unknown IRES sequences is certainly still very large.

IRES-like elements are also cis-acting sequences able to mediate internal entry of the 40S ribosomal subunit on some eukaryotic and viral messenger RNAs upstream of a translation initiation codon. Unlike IRES elements, in IRES-like elements, the Yn-Xm-AUG unit (Y, pyrimidine; X, nucleotide), which appears essential for IRES function, is not required.

The constructs disclosed herein can optionally comprise IRES or IRES-like elements. For example, the constructs disclosed herein can further comprise an element between the first and second nucleic acid sequences wherein the element provides differential expression two or more driver element or reporter element sequences. In a further example, the element between the two or more driver element or reporter element sequences can be an internal ribosomal entry site or an internal ribosomal entry site-like element. In a further example, the constructs disclosed herein can further comprise an element between the first or second two or more driver element or reporter element sequences and the third two or more driver element or reporter element sequence, wherein the third two or more driver element or reporter element sequence is not located between the first and second two or more driver element or reporter element sequences, and wherein the element provides differential expression between the first or second two or more driver element or reporter element sequences and the third two or more driver element or reporter element sequence.

The IRES or IRES-like element can be naturally occurring or non-naturally occurring. Examples of IRESs include, but are not limited to the IRES present in the IRES database at ifr31w3.toulouse.inserm.fr.IRESdatabase/. Examples of IRES can also include, but are not limited to, the EMC-virus IRES, or HCV-virus IRES. In addition, the IRES or IRES-like element can be mutated, wherein the function of the IRES or IRES-like element is retained.

In an aspect, the first strand can comprise a 5' ARM, one or more linkers, one or more GADE sequences (or a GADE library), a barcode, and a nucleic sequence complementary to the 3' ARM on the second strand. Generally, linker sequences disclosed herein can be nucleic acid sequences that can connect nucleic acid sequences (e.g., one nucleic acid to another (e.g., a second nucleic acid sequence) nucleic acid sequence).

In an aspect, the first strand can comprise a 5' ARM. In an aspect, the 5' ARM can be identical to (or identical to a portion of), for example, an integration or insertion site (e.g., an adeno-associated virus integration site (AAVS1) locus). The AAVS1 gene can serve as a safe harbor site and the desired target or location for the insertion of DNA that permits stable expression of desired nucleic acids and does not interfere with host processes. In an aspect, the 5' ARM can be homologous to AAVS1 locus. In an aspect, the 5' ARM can flank the desired insertion site for homologous recombination. The 5' ARM, located on the first strand, can be complementary to a corresponding portion of the second strand. The 5' ARM and the 3' ARM on the second strand (see below) can be nucleic acid sequences wherein each arm flanks a site for insertion (e.g., GADE and/or GARE sequences. In an aspect, the first strand can comprise a 3' ARM. In an aspect, the 3' ARM can be identical to or identical to a portion of an AAVS1 locus. In an aspect, the 5' ARM and 3' ARM of the first strand flank the GADE and GARE sequences. In an aspect, the 5' ARM can comprise a Flox sequence (e.g., for cre-lox system). Examples of integration sites include but are not limited to FLP-FRT system (flanking Flp Recombination Target), Jump-In™ Fast Gateway® System (pseudo attP sites), Piggybag tranpososon system (TTAA chromosomal sites), phage integrase (in the att sites). In addition, gene editing endonucleases like CRISPR Cas-9, TALEN, Zinc Finger Nucleases (ZFNs), etc. can use any portion of DNA as flanking ARMs if the site of the double-strand break for site specific integration is present between the flanking ARMs.

In an aspect, the first strand can also comprise a first linker sequence. The first linker sequence can be a nucleic acid sequence complementary to a selectable marker. The selectable marker can be located on the s the second strand. In an aspect, the first linker sequence can be between the 5' ARM and a GADE sequence. In an aspect, the first strand comprises a first linker sequence between the 5' ARM and the GADE sequence wherein the first linker sequence can be complementary to the selectable marker of the second strand.

In an aspect, the first strand can comprise a second linker sequence. The second linker sequence can be a nucleic acid sequence located between the barcode sequence (e.g., first barcode) and a nucleic acid sequence that can be complementary to the 3' ARM located on the second or opposite strand. In an aspect, the second linker sequence can be complementary to a GARE sequence of the second strand. In an aspect, the first strand can comprise a second linker sequence between the GADE sequence and the 3' ARM.

In an aspect, the first stand can comprise a nucleic sequence complementary to the 3' ARM on the second strand (e.g., opposite strand). In an aspect, this nucleic acid sequence can be referred to as a first nucleic acid sequence. In an aspect, the first nucleic acid sequence can be located on the first strand.

In an aspect, the first strand can comprise a nucleic acid sequence that can comprise or encodes functional sequences (e.g., sequences generally found in plasmid). Said functional sequences can be referred to as a linker (e.g., a third linker; a third linker on the first strand). Such functional sequences are known to one of ordinary skill in the art. Examples of standard sequences include but are not limited to origin of replication and all of its control elements and an antibiotic resistance gene. The third linker can be located between the first nucleic acid sequence (e.g., on the first strand) and the 5' ARM.

In an aspect, the first or second linker of the first strand can comprise a transcriptional control element and a selectable marker.

In an aspect, the second strand can comprise a 3' ARM, one or more linkers, one or more GARE sequences (or a GARE library), a barcode, a selectable marker, and a nucleic sequence complementary to the 5' arm on the second strand.

In an aspect, the second strand can comprise 3' ARM. In an aspect, the 5' ARM and the 3' ARM can be the same or different. In an aspect, the 3' ARM can be homologous to, for example, an integration or insertion site (e.g., a AAVS1 locus). In an aspect, the 3' ARM can be identical to a portion of the AAVS1 locus. The AAVS1 gene can serve as a safe harbor site and the desired target or location for the insertion of DNA that permits stable expression of desired nucleic acids. In an aspect, the 3' ARM can flank the desired insertion site for homologous recombination. The 3' ARM, located on the second strand, can be complementary to a corresponding portion of the second strand. The 3' ARM and the 5' ARM on the first strand can be nucleic acid sequences wherein each arm flanks a site for insertion. In an aspect, the 5'ARM and the 3'ARM of the second strand can flank the GADE and GARE sequences. In an aspect, the second strand comprises a 5' ARM. In an aspect, the 5' ARM can be identical to or identical to a portion of an AAVS1 locus.

In an aspect, the second strand can also comprise a first linker sequence. In an aspect, the linker sequence can be a first linker on the second strand. The linker sequence can be a nucleic acid sequence that can be the reverse complement to the GADE sequence. In an aspect, the first linker sequence can be between the GARE sequence and a selectable marker. In an aspect, the second strand can comprise a first linker sequence between the GARE sequence and the 5'ARM, wherein the first linker sequence of the second strand can be complementary to the GADE sequence of the first strand. In an aspect, the second strand can comprise a first linker sequence between the GARE sequence and the selectable marker, wherein the first linker sequence of the second strand can be complementary to the GADE sequence of the first strand. In an aspect, the linker of the second strand can comprise a transcriptional control element and a selectable marker.

In an aspect, the second stand can comprise a nucleic sequence complementary to the 5' ARM on the first strand. In an aspect, this nucleic acid can be referred to as a second nucleic acid sequence. In an aspect, the second nucleic acid sequence can be located on the second strand.

In an aspect, the second strand can comprise a nucleic acid sequence that can comprise sequences that are complementary to the nucleic acid sequences that encode the functional sequences (e.g., regulatory sequences generally found in plasmid). Said functional sequences can be referred to as a linker (e.g., a second linker; a second linker on the second strand). In an aspect, the second linker can be located between the second nucleic acid sequence (e.g., on the first strand) and the 3' ARM.

In an aspect, the first or second strand can comprise a selectable marker. In an aspect, the second strand can comprise a selectable marker. In an aspect, the second strand can comprise a nucleic acid encoding a selectable marker. The selectable marker can be any protein or nucleic acid sequence that can be detected, including, for example, antibiotic resistance. The selectable marker can be used to select for the cells, for example, that comprise a sequence of interest. Examples of suitable selectable markers for mammalian cells can be dihydrofolate reductase gene (DHFR), thymidine kinase gene, amino 3'-glycosyl phosphotransferase (neo gene), hygromycin B phosphotransferase (Hph gene), blasticidin S deaminase, bleomycin-resistance (bleoR) gene, and puromycin N-acetyl-transferase (pac gene). In an aspect, the selectable marker is a puromycin N-acetyl-transferase gene. Other useable genes are selectable antibiotic resistance genes (e.g. the neomycin phosphotransferase gene) or drug resistance genes (e.g. the multidrug resistance (MDR) genes), and the like. In an aspect, the selectable marker can be a fluorescent protein. In an aspect, the selectable marker can be GFP or red fluorescent protein (RFP). Examples of additional selectable markers that can be useful in the claimed methods and compositions can be found in "Design and application of genetically encoded biosensors," Palmer et al., Trends in Biotechnology, March 2011, Vol. 29, No. 3; "Novel uses of fluorescent proteins," Mishin et al., Current Opinion in Chemical Biology, 2015, 27:1-9; and Proc Natl Acad Sci USA; 2016 Mar. 1:113(9): 2388-93; doi: 10.1073/pnas.1600375113, which are incorporated by reference in their entirety.

In an aspect, the first and second strands can comprise functional sequences between the 5' end of the 5'ARM of the first strand and the 3' end of the 3'ARM of the first sequence and between the 3' end of the 5'ARM of the second strand and the 5' end of the 3'ARM of the second sequence. In an aspect, said functional sequences can be complementary to each other. In an aspect, the functional sequences can comprise an origin of replication sequence, an antibiotic resistance marker, a nuclear localization signal-encoding nucleic acid sequence and multiple cloning sites. In an aspect the encoded nuclear localization signal can be SV40.

A functional sequence can be a genetic element responsible for the replication of plasmids during cell growth and division such as a replication origin (also "origin of replication" or simply "origin"). There are several different replication origins and they differ in their plasmid copy number per cell (e.g., how many molecules of the plasmid are maintained in the cell), mechanism of copy number control, cell-to-cell copy number variation, and even the degree of coiling of the physical DNA.

At the most basic level, function of the antibiotic resistance marker is to allow the bacterial cell to grow even in the presence of a particular antibiotic. Plasmid backbones include antibiotic resistance markers because the markers allow you to select for cells that contain your plasmid. When E. coli cells grow and divide, plasmids can inadvertently be lost from the cell. In some cases, cells without a plasmid can potentially grow faster than cells with the plasmid which means that cell cultures can quickly become dominated by plasmid-free cells. Thus, cells which don't have a copy of the plasmid are killed by antibiotic present. Common antibiotic resistance markers are enzymes that confer resistance to ampicillin ("Amp" or A), kanamycin ("Kan" or K), chloramphenicol ("Cm" or C) and tetracycline ("Tet" or T).

Disclosed herein are GigaAssay driver element (GADE) libraries (GADEL). GigaAssay driver element libraries (GADELs) can comprise a promoter and a driver element to express a library or single clone that can then be tested by a Giga Assay reporter element (GARE) library. In some aspects, the promoter element can be constitutive or inducible (Qin et al., 2010). In some aspects, the driver element libraries (e.g., GADE libraries) can comprise, for example, chimeric minimotif decoy (CMD) clones to inhibit molecular functions (e.g, CMD clones are combinations of short peptide motifs that can be decoy inhibitors; Balla et al., 2006; Puntervoll etl., 2003; Vyas et al., 2009), silencing RNAs or CRISPR/Cas libraries for each gene in a genome to block gene function (Joung et al., 2017; Seyhan et al., 2005; Wong et al., 2016), transcriptional decoy libraries to probe transcriptional elements (Mann and Dzau, 2000), microRNA libraries to probe their role in cells (Ujihira et al., 2015), enhancer or insulator element libraries, pseudogene libraries, any sequence-based library based on its functional elements. Other libraries can include, for example, cDNAs for all genes in the genome to test for sufficiency or regions of genes (e.g., domains, sets of domains, or genes with domains deleted) to probe or examine gene function and the function of alternatively spliced transcripts. Yet other libraries can be used to test for requirements of individual amino acids in genes. For example, a gene (e.g., BRCA1) can be randomly mutated with a chemical mutagen (e.g., EMS), error prone PCR, or gene synthesis to generate a library comprising up to 100 M+ or more mutants of the gene to test for a specific outcome of each mutant. In some aspects, the targeted libraries can also be used along with subsets or combinations of any of the libraries disclosed herein. In some aspects, the additional libraries (or types of libraries) can be generated depending on the question being asked.

In an aspect, the GADE sequences can comprise a transcriptional control element (e.g., a promoter), driver element and a 3' UTR. In an aspect, the transcriptional control element can be any promoter or enhancer. In an aspect, the promoter can be any human promoter. The transcriptional control element can be constitutively active or regulatable. The transcriptional control element can be operably linked to the driver element. The transcriptional control element of the first strand can be the same or different than the transcriptional control element of the second strand. In an aspect, the transcriptional control element can be CMV. In an aspect, the driver element can be cDNA. The driver element can be multiple cDNAs. The driver element can be microRNA. The driver element can be a DNA nucleic acid sequence. In an aspect, the driver element can be tat. The driver element can encode any sequence of interest. In an aspect, the driver element can be one or more sequences of interest. If the driver element comprises two or more sequences of interest, each driver element sequence can be separated by an internal ribosome entry site (IRES). Accordingly, the driver element can comprise one or more IRES. For example, a GADE sequence can encode three cDNAs, wherein in each cDNA can be separated by an IRES, each producing single transcripts, generating multiple proteins. In an aspect, any of the above can be a GADE library used in the GigaAssay disclosed herein. In the case of a GADE library, multiple vectors can be generated such that each vector comprises a different GADE sequence.

In an aspect, the GADE sequence can comprise from 5' to 3' a transcriptional control element operably linked to one or more driver elements and a 3'UTR. In some aspects, the UTR region consists of a synthetic polyA tail, a barcode sequence and a SVpolyA tail. Preparing the UTR region is within the abilities of one of ordinary skill in the art. For example, the synthetic polyA tail can be synthesized from oligos (e.g., Sigma Alrich), barcode sequences can be synthesized from Genelink, and SVpolyA tail can be amplified from, for example, the pm-CherryC1 plasmid. The 3'UTR can comprise a barcode sequence. In an aspect, the barcode sequence of the GADE sequence can be complementary to a barcode sequence in the 3' UTR of the GARE sequence. As disclosed herein, the 3' UTR of the GADE sequence can comprise one or more barcode sequences.

In an aspect, the double-stranded nucleic acid constructs can comprise one or more driver elements. In an aspect, the one or more driver elements can be DNA, cDNA, RNA, microRNA, siRNA, an shRNA, or an mRNA. In an aspect, the one or more driver elements can be any set or any set of sequences that can be grouped or characterized as being in a class (e.g., genomic DNA library). In an aspect, the GADE sequences disclosed herein can comprise two or more driver elements. In an aspect, the two or more driver elements can be separated by one or more IRES elements.

Also disclosed herein are GigaAssay reporter elements. In some aspects, each GADE library can be assayed by a GigaAssay reporter element (GAREs) or GARE library. In some aspects, the GARE libraries are reporters comprising a promoter, leader sequence, expression reporter, and 3'UTR elements. Each of these elements can be a single entity or a library of entities. In some aspects, the promoter element can encode, for example, a promoter that can be overexpressed including but not limited to CMV, all promoters in a genome, all promoters of a certain type (e.g., viral). Any single or set of promoters can be mutagenized to create a library, or libraries, that can be generated for a different part of the promoter including but not limited to transcription factor binding sites, insulators, and enhancers. GARE libraries can also have variable leaders, and 3' UTR sequences.

The GARE can be any type of fluorescent or reporter protein that can be transcribed and/or translated. The reporter is not limited to a protein. For example, the reporter can be any other type of DNA sequence that can be transcribed. A GARE library can also be designed or created such that the GARE library comprises reporters to provide up to 100M+ assays. An example of a GARE library can be, for instance, a library comprising all gene promoters, gene promoters in a genome driving GFP expression in the reporter position that can be used to test the expression output of all promoters in a genome in a single experiment. Another variation can be to use a selectable marker as a reporter. In an aspect, the GigaAssay can also be coupled with a selection step for the selectable marker beyond the selection for GigaAssay cassette integration.

In an aspect, the GARE sequence can comprise from 5' to 3', a transcriptional control element operably linked to one or more reporter elements and a 3'UTR. In an aspect, the 3'UTR can comprise a barcode sequence. In an aspect, the barcode sequence of the GARE sequence can be complementary to a barcode sequence in the 3' UTR of the GADE sequence. As disclosed herein, the 3' UTR of the GARE sequence comprises one or more barcode sequences.

In an aspect, the GARE sequence can comprise a transcriptional control element, a reporter element and a 3' UTR. In an aspect, the transcriptional control element can be any transcriptional control element. In an aspect, the transcriptional control element can be any human promoter. The transcriptional control element can be constitutively active or regulatable. The transcriptional control element of the second strand can be the same or different than the transcriptional control element of the first strand. The transcriptional control element can be operably linked to the reporter element. In an aspect, the transcriptional control element can be CMV. A single transcriptional control element can drive more than one reporter element. The reporter element can be a variable that can be changed. In an aspect, the reporter element can be GFP. In an aspect, the reporter element can be any detectable nucleic acid sequence. The detectable nucleic acid sequence does not need to be known. In an aspect, the reporter element can be a fluorescent protein (e.g., green fluorescent protein (GFP), mCherry). In an aspect, the reporter element can be a RNA. In this case, the reporter element activity can be a quantitative measure of the transcripts. In some aspects, the reporter element can be an enzyme (e.g., chloramphenicol acetyltransferase (CAT), alkaline phosphatase (AP), β-galactosidase (β-gal), luciferases, and β-lactamase, and β-glucoronidase). In an aspect, the reporter element can be one or more sequences that can be detected. If the reporter element comprises two or more sequences of interest, each sequence can be separated by an IRES. Accordingly, the reporter element can comprise one or more IRES. For example, a GARE sequence can encode three detectable proteins, wherein each of the nucleic acids that encode the corresponding detectable proteins can be separated by an IRES, each producing a single transcript that generates multiple proteins. In an aspect, a GARE library can be used in the GigaAssay disclosed herein. In the case of a GARE library, multiple vectors can be generated such that each vector comprises a different GARE.

In an aspect, the double-stranded nucleic constructs disclosed herein can comprise one or more reporter elements.

In an aspect, the GARE comprises two or more reporter elements. In an aspect, the two or more reporter elements can be separated by one or more IRES elements.

Disclosed herein are selectable markers. In an aspect, the selectable markers can be located on either the first strand or the second strand of the constructs disclosed herein. In an aspect, the second strand further comprises a selectable marker. In an aspect, the selectable marker can be dihydrofolate reductase, thymidine kinase, amino 3'-glycosyl phosphotransferase (neo gene), hygromycin B phosphotransferase (Hph gene), blasticidin S deaminase, bleomycin-resistance (bleoR) gene, and puromycin N-acetyl-transferase (pac gene). In an aspect, the selectable marker can be puromycin N-acetyl-transferase.

Selectable markers can also be used to identify those cells comprising (or that have integrated) a sequence of interest or, as described herein, the presence of a double-stranded nucleic acid construct as disclosed herein. For example, a light-generating protein can be used.

Any technique that can be used to introduce the nucleic acid constructs to cells can be employed. A variety of transformation techniques are well known in the art. Methods that can be used to introduce nucleic acids or constructs into the cells of choice include, but are not limited to direct microinjection into nuclei, transfection, electroporation, VAULTs, gold particle, bombardment.

Disclosed herein are double-stranded nucleic acid constructs comprising transcriptional control elements. In an aspect, the transcriptional control element of the GARE sequence can be the same as the transcriptional control element of the GADE sequence. In an aspect, the transcriptional control element of the GARE sequence can be the different than the transcriptional control element of the GADE sequence. In an aspect, the transcriptional control elements can be selected from the group consisting of a promoter or an enhancer, or insulator. Examples of suitable promoters include but are not limited to mH1 promoter, a hH1 promoter, a CAG promoter, a CMV promoter, a CMV based promoter, a chicken β-actin promoter, Ubiquitin C promoter, or an EF-1α promoter. In an aspect, the transcriptional control element can be inducible or regulatable.

Disclosed herein are barcodes or barcode elements. A barcode can be used to match a single clone of a GADE library with a single code of a GARE library. In some aspects, the same barcode can be produced by the transcript for each GADEL clone and each GAREL clone originating from a single vector or the same transfected cell. In some aspects, the barcode allows the source of these clones to be identified, for example, as coming from the same clonal cell group that can be used in any subsequent analysis. In some aspects, the barcodes, as described herein, can be encoded on the same strand, or as in the case presented in FIG. 1, on opposing strands. When the barcodes are present in the opposing strand, each GADE clone barcode can be the reverse compliment of the GARE barcode on the other stand, or vice versa. In some aspects, the barcode can be of any length sufficient to provide the combinatorial complexity that exceeds that needed for the library being tested.

In an aspect, the barcode on the first strand can comprise a nucleic acid sequence that can be a specific relatively short sequence. The barcode or barcode sequence can be used to identify a sample (e.g., a plasmid or cell). In an aspect, the barcode sequence on the first strand can be referred to as the first barcode sequence. The barcode sequence can match or bind to a nucleic acid found on the opposite strand. In an aspect, the first barcode sequence located on the first strand can anneal to the second barcode sequence located on the second strand. In an aspect, the barcode can be used to identify the GADE (e.g., located on the first strand) and the GARE (e.g., located on the second strand) from the construct (e.g., plasmid construct; same cell). The first barcode sequence can be located between the GADE and a linker (e.g., second linker).

In an aspect, the barcode sequence on the second strand can comprise a nucleic acid sequence that can be a specific relatively short sequence. The barcode sequence can be used to identify a sample (e.g., a plasmid or cell). In an aspect, the barcode sequence on the second strand can be referred to as the second barcode sequence. The barcode sequence on the second strand can be the reverse complementary sequence that can anneal to a nucleic acid found on the opposite strand (e.g., first strand). In an aspect, the second barcode sequence located on the second strand can anneal to the second barcode sequence located on the first strand. In an aspect, the barcode can be used to identify a GADE sequence (e.g., located on the first strand) and a GARE sequence (e.g., located on the second strand) from the construct (e.g., plasmid construct; same cell). The second barcode sequence can be located between the GARE and a linker.

In an aspect, the GADE and GARE sequences both can comprise a barcode sequence. In an aspect, the barcode sequence of the GADE sequence can be complementary to the barcode sequence of the GARE sequence.

Disclosed herein are cell lines. In an aspect, the cell line can comprise the double-stranded nucleic acid constructs disclosed herein. In an aspect, the cell line can comprise the vectors disclosed herein.

Disclosed herein are methods of making a cell line described herein. Standard gene editing techniques can be used to create a cell line that can be useful in the compositions and methods disclosed herein. In an aspect, the cell line can be a transgenic cell line. In an aspect, the method of making a transgenic cell can include introducing one or more of the double-stranded nucleic acid constructs disclosed herein (or vectors disclosed herein) to a diploid cell. The 5' and 3' ARMSs described herein can be designed to insert into one allele of a heteroallelic locus or into cells that are haploid. This could by the Y or X chromosome in a male mammalian cell. In an aspect, the method can include integration of one or more GigaAssay Cassettes disclosed herein into a cell. The cells can be engineered to have one intact allele of any heteroallelic locus. Methods of engineering said cells are known to one of ordinary skill in the art.

In an aspect, the methods can further include the step of selecting cells based on the presence of the selectable marker. In an aspect, the methods disclosed herein can also include separating the cells by flow sorting.

In an aspect, the methods can further include adding a test agent or test compound to the selected cells (or contacting or exposing one or more of the cells with a test agent or test compound). Examples of test agents or test compounds include but are not limited to hormones, therapeutic agents, receptor agonists, receptor antagonists, receptor inhibitors, and toxins. In an aspect, the methods can include the step of analyzing the cells for an effect by the test agent or test compound. The type of question will dictate which test agent or test compound can be used. The type of effect will depend on the test agent of test compound. In some aspects, the choice of the test agent or test compound and the effect is within the skill of a person in the art. In an aspect, the effect can be to turn on or activate the one or more reporter elements. Measuring the effect of one or more of the reporter elements within the cell is known to a person of ordinary skill in the art. In some aspects, the effect of the test agent or test compound can be a change (increase or decrease) of the expression of the one or more reporter elements.

Figure 8:
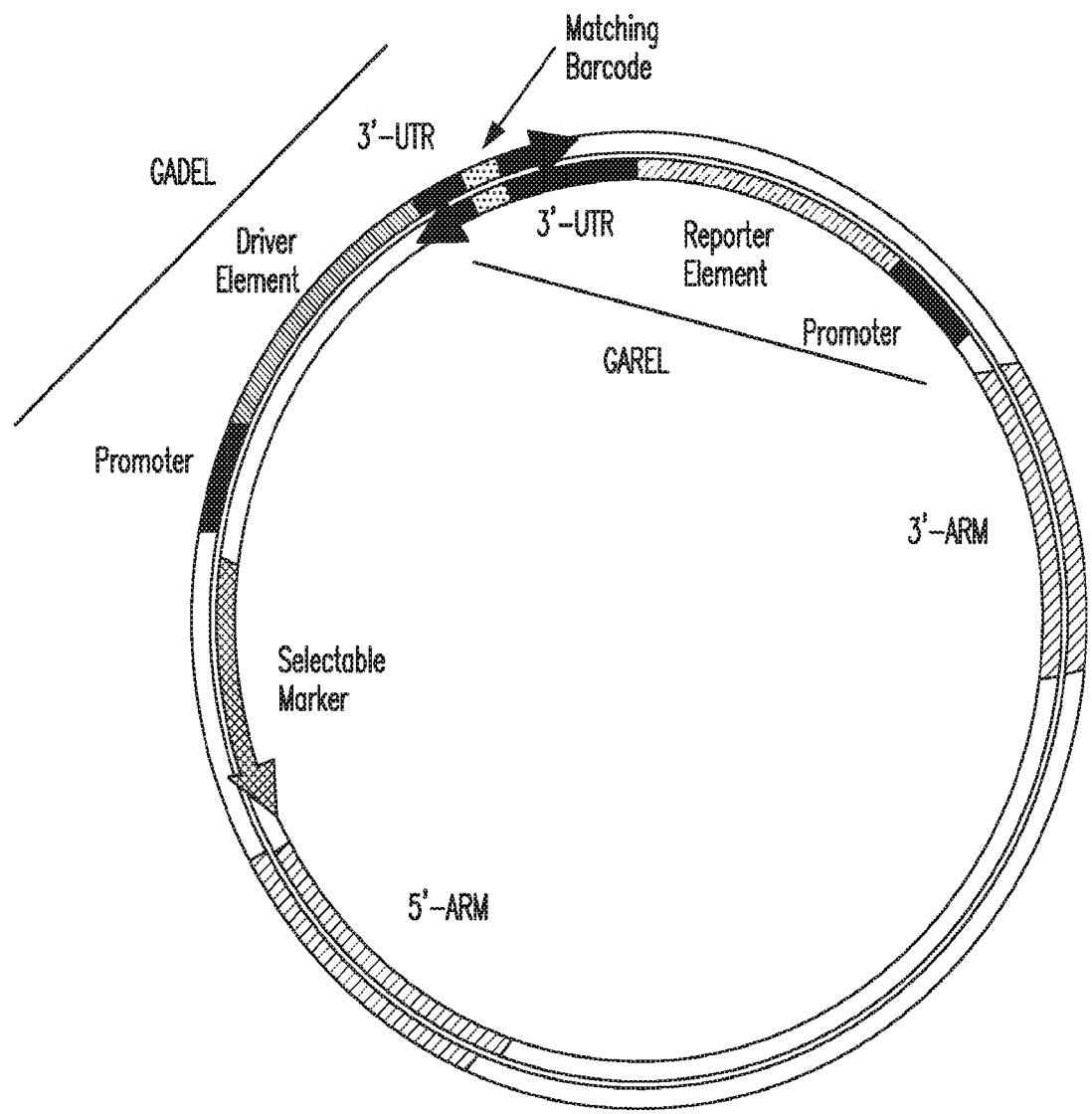
FIG. 8 shows an example of a disclosed vector.

Many different types of vectors can be used in the compositions and methods described herein. Any type of general expression vector can be used. In some aspects, the GigaAssay vector or construct as described herein can comprise a selection marker, constitutive promoter, one or more cloning sites, origin of replication, 5' ARMs for integration into an insertion site of a target locus (e.g., a safe harbor locus), and a GigaAssay cassette. In some aspects, the GigaAssay cassette can be one of many different versions. FIG. 1A and FIG. 8 provide examples of a GigaAssay cassette and GigaAssay vector. The GigaAssay cassette and the GigaAssay vector are not limited to the version in FIG. 1A. In some aspects, the GigaAssay cassette can comprise a promoter that drives expression of a GADE library or single GADE, wherein the GADE comprises a 3'UTR, wherein the 3' UTR comprises a barcode and polyadenylation (poly(A)) signal. In some aspects, the cassette, as described herein, can also comprise a GARE on the opposite strand that has a promoter that drives expression of a GARE library or a single GARE and a 3' UTR that overlaps the part of the 3' UTR of the GADE library encoded on another strand that contains the barcode. Thus, the construct described, for example in FIG. 1A, can express two different RNAs, one comprising a first sequence, and one comprising a second sequence, wherein, part of the second sequence is the reverse compliment of part of the first sequence. Together, the first sequence and second sequence form the barcode duplex as described herein. In other words, the construct can comprise one RNA molecule that comprises the barcode and a second RNA molecule that comprises the reverse complement of the same barcode. In some aspects, the GigaAssay cassette can be bounded or flanked on both ends by ARMS for integration into an insertion site of a target locus (e.g., a safe harbor locus), and a GigaAssay cassette.

As disclosed herein, FIG. 1A shows an example of the GigaAssay vector. In an aspect, the vector comprises two double-stranded ARMS that can be identical with (or identical to a portion of) the desired insertion site in the genome. In an example using human cells, the AAVS1 safe-harbor locus can be used. In an aspect, the vector can also encode the expression of a driver transcript (GADE) and a reporter transcript (GARE) wherein the GADE and GARE contain a complementary barcode in their 3' UTRs of opposite strands.

As disclosed herein, FIG. 1B shows an example of the GigaAssay workflow (e.g., method). The GigaAssay workflow can include the step of generating a cell line. In an aspect, a specific clone from a library of vectors can be introduced into a single cell, and a population of stably integrated recombinants can be identified using a selectable marker. Optionally, cells can be treated and/or flow sorted by flow cytometry as a step to select cells that respond in a desired way or have a specific effect. RNA can be isolated and cDNA can be prepared from the GARE and GADE transcripts (libraries). NGS and analysis can determine the identity and expression levels of these transcripts.

The disclosed GAREs, GADEs, GARE libraries and GADE librariess can be used in combination with each other in many ways. Any of the vectors or GigaAssay cassette elements other than the barcode can also be mutagenized to create a library that can be tested. In some aspects, a GigaAssay cassette can be designed to be flexible and to form a flexible system that can be used (e.g., workflows) to answer different scientific questions. Table 1 includes general and specific non-limiting examples of GigaAssay cassettes and ultimately the GigaAssay methods in which current technologies or methods cannot accomplish.

TABLE 1

Examples of GigAssay Cassettes and Uses Thereof

| Question | GADEL Promoter | GADEL Driver | GAREL Promoter | GAREL Reporter | Treatment | Flow Sort |
|---|---|---|---|---|---|---|
| Which genes are sufficient to stimulate a CREB transcription reporter? | CMV | Full length Gene cDNA library | CREB or other response element | GFP | none | no |
| Which genes are necessary to stimulate a transcriptional reporter? | CMV | siRNA library | CREB or other response element | GFP | Hormone that stimulates CREB | no |
| Which genes affect CREB transcription? | CMV | Full length cDNA gene expression library | gDNA fragment library- CREB response element | GFP | none | no |
| Which transcription factors are involved in apoptosis? | CMV | Full length cDNA gene expression library | Weak constitutive promoter | Caspase 3 | none | no |
| Which microRNAs inhibit expression of which genes? | CMV | MicroRNA library | CMV | Full length Gene cDNA library with promoters | none | no |

TABLE 1-continued

Examples of GigAssay Cassettes and Uses Thereof

| Question | GADEL Promoter | GADEL Driver | GAREL Promoter | GAREL Reporter | Treatment | Flow Sort |
|---|---|---|---|---|---|---|
| Which BRCA1 gene variants effect on homologous recombination or NHEJ? | CMV | EMS mutagenized BRCA1 cDNA library | CMV | Homologous recombination and NHEJ mCherry/GFP reporters | CRISPR/Cas or TALEN | no |
| Which BRCA1 gene variants fold correctly? | CMV | Mutagenized BRCA1-GFP chimera cDNA library | | | | yes |
| Identify all enhancers or insulators, and the genes they effect | CMV | Full length cDNA gene expression library | gDNA fragment library | GFP | none | possibly |
| Which indels affect gene function? | CMV | Indel mutagenizes of BRCA1 cDNA library | CMV | Homologous recombination and NHEJ GFP reporters | CRISPR/Cas or TALEN | no |
| Which pseudogenes regulate the RNA level of homologous gene? | CMV | Pseudogene expression library | Weak constitutive promoter | Gene expression library | none | no |
| Which pairs of transcription factor synergize to drive transcription? | CMV | Transcription factor library-IRES-transcription factor library | CMV | Library of transcriptional reporters. | No | no |
| Which genes are required for viral gene expression in different viruses ? | CMV | human siRNA library | Library of viral LTRs- | GFP | none | possibly |
| Which genes are required to change membrane potential that also change intracellular Cl⁻ ? | CMV | human siRNA library | CMV | Voltage sensitive GFP-IRES-Chloride analyte GFP sensor | None | no |
| Which pairs of transcription factors that change membrane potential that also change intracellular Cl⁻ ? | CMV Transcription factor library-IRES-transcription factor library | CMV | Voltage sensitive GFP-IRES-Chloride analyte GFP sensor | None | no | |
| Which leaders for maximize gene expression? | None | none | CMV | Randomly mutagenized Transcript leader library-GFP | None | none |

In some aspects, the GigaAssay can use combinations of GARE libraries and GADE libraries with different cell treatments, and cell sorting protocols. A non-comprehensive set of general and specific example combinations are shown in Table 1. An experiment, for example, can be designed using a single GADE with a library of GAREs, a single GARE with a library of GADEs. In an aspect, the GigaAssay can assess all genes that activate a transcriptional reporter of interest (Green et al., 2005; Jiang et al., 2008). Alternatively, both the GADE and GARE can each be a library. For example, an experiment can be carried out that tests which constitutively overexpressed genes activate which promoter in a library of mammalian promoters driving GFP expression (Kain et al., 1995). If desired, multiple (e.g., 2-6) GAREL and/or GADEL can be examined in the same experiment through use of an internal ribosomal entry site (IRES) (Gurtu et al., 1996). When an IRES is used, the NGS can also include long or paired end reads to sequence the entire transcript. As described above and an important aspect of the design is that the RNAs produced from the GADE library and GARE library each comprise a matching barcode that was specifically produced from the same starting cell or its progeny. As shown in FIG. 1A, Generally, this can be done by placing the barcode in the 3' UTR, which can be encoded by both transcripts produced from opposite strands on the DNA. To avoid, eliminate, reduce or minimize artifacts from degeneracy, the number of specific barcodes must exceed the combinatorial complexity of the library constructed. This can be relevant for many of the steps in the construction of a library.

Disclosed herein are assays that can involve one or more of the following steps: introducing the construct (e.g., cassette) into a model system (e.g, cells), integration, selection, treatment, PCR and RNAseq or NGS. In some aspects, the GigaAssay cassette can be introduced into cells or animals by standard transfection and infection techniques including but not limited to lipid based transfection or infection with a recombinant integrase-defective lentivirus. A poison or auxotrophic marker (eukaryotic cells) or antibiotic resistance gene (bacterial cells) can be used as a selection marker for generating a heterogeneous cell population with the stably integrated library. To achieve this, CRISPR/Cas targeting using the AAVS1 or other safe-harbor locus, for example, can be used followed by selection to generate GigaAssay cassettes integrated into cells by homologous recombination using a selectable marker. Cells can then be treated at various times, with one or more treatments, doses, etc. to test the question being asked (see, for example, Table 1). If the reporter, for example, is a fluorescent protein or is part of a fluorescent assay, flow cytometry can be used to sort cell populations. Cells can then be harvested, RNA extracted and converted to dsDNA by standard techniques (e.g., molecular biology techniques) known to one of ordinary skill in the art. Genomic DNA can also be extracted. PCR can be used to generate NGS libraries from the GADE and GARE RNAs. Libraries can then sequenced by NGS. The assays described herein (see, FIG. 1) can be used for single cells, or larger numbers of organisms. In some aspects, the assay disclosed herein can be used for up to billions of cells.

In an aspect, a GigaAssay plasmid construct comprises the following: at least two ARMS (e.g., 3' ARM and a 5' ARM), wherein the two ARMS flank the DNA (or nucleic acid sequence) of interest, wherein the DNA (or nucleic acid sequence) of interest can be introduced or integrated at a specific insertion site of a target locus (e.g., a safe harbor locus); encoded GADE and GARE; a specific barcode that is complementary to the identity of the GADE and GARE from the same plasmid construct, thus the same cell; for example, in a double-stranded DNA molecule, a first strand comprises a specific first barcode and a second strand comprises a second barcode that is matching or complementary to the first barcode; and a selectable marker that can be antibiotic resistance for selection of cells (e.g., to confirm the insertion of a GIGA Assay cassette or can be used for selection of bacterial cells during library construction).

In an aspect, a GigaAssay plasmid can comprise a GADE and a GARE. GADE activity can be measured as readout of the GARE. Mutant libraries of GADEs can provide a different readout for their respective GAREs and can serve as a measure of their activity. It is important to align the GADE and GARE within the same plasmid by their specific and complementary barcodes. The GADE (coded by the external DNA strand in FIG. 1A) and GARE (coded by the internal DNA strand in FIG. 1A) can be placed within the GigaAssay cassette in such a way that the 3'UTR from both the transcripts overlap. A specific barcode can be present within this overlap region, but in the opposite direction (see arrows in FIG. 1A). Therefore, the specific barcode sequence in the GADE can be the reverse complement of the barcode sequence present in the GARE.

Disclosed herein as an example of the GigaAssay vector design shown in FIG. 1A, the assembly of the following. The pAAVS1-puro-DNR (GE100024, Origene) plasmid was constructed with flanking arms (AAVS1-left and AAVS1-right) for genomic integration. For the Tat/LTR-GFP GigaAssay vector, the coding sequence of wild type/mutant Tat (wtTat/mTat) was cloned between the EcoRI and KpnI sites. The poly(A) sequence of SV40 origin for the Tat sequence was inserted between AscI and MluI. The HIV LTR and GFP were PCR amplified independently and fused together by overlap extension PCR to generate LTR-GFP. LTR-GFP was cloned between the NotI and MluI site such that their reading frame was from the bottom strand of DNA in 5' to 3' direction. The synthetic poly(A) sequence for the GFP transcript was cloned between KpnI and AsiSi(SgfI) with its reading frame from the opposing bottom strand of DNA. Specific 32mers barcodes were cloned into AsiSi and AscI sites of the randomly mutated Tat-GigaAssay library (FIG. 1A). Templates for PCR amplification were pNL4-3 ΔE-eGFP for the HIV Tat and LTR, and peGFP-C3 for GFP.

Sequencing reads can be analyzed to match GADE and GARE library clones and to determine the expression levels of the clones. This can be accomplished by using an informatics program that reads the FASTQ file produced from the NGS run. The output can identify a GADE-GARE pair with expression levels for each clonal cell group analyzed. This high-throughput assay can analyze each clonal cell group individually in a population of up to a billion single cell assays in a single experiment. The report can be organized in different ways, statistically analyzed, and processed with other bioinformatic data depending on the experimental design. A plugin style platform can be created to accommodate different experimental workflows for this assay. Interpretation of the results can be, for example, that the driver affects the reporter while the treatment or other type of manipulation can also be examined.

In some aspects, a GigaAssay can provide a higher standard for rigor and reproducibility. The GigaAssay can use NGS to measure a high number of independent replicates (e.g., n is approximately 10-1000 for each measurement) and it measures both positives and negatives, thus rigorous statistical metrics of sensitivity, specificity, accuracy, and positive predictive value (PPV) can routinely be assessed.

Figure 2:
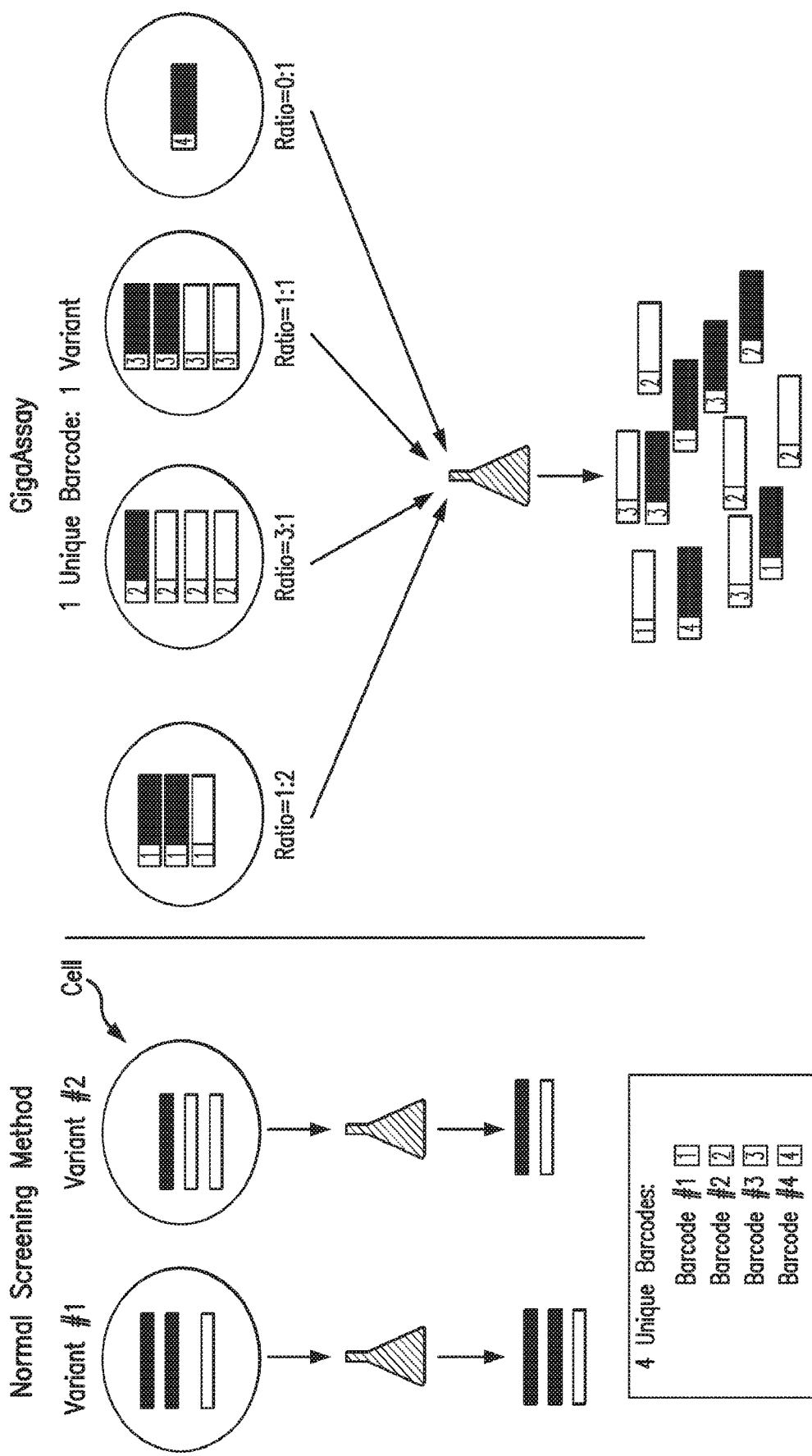
FIG. 2 shows an advantage of using the disclosed methods in view of existing screening methods.

The GigaAssay and its analysis as disclosed herein have several advantages over existing technologies including but not limited to measuring a functional readout; measuring single cells in a population separately (FIG. 2); exploring several variables simultaneously; producing many independent replicates; and assessing both negatives and positives.

Disclosed herein are methods of preparing one or more cells for analysis (see, FIG. 1B). In an aspect, the methods can include introducing one of the double-stranded nucleic acid constructs (or vectors) disclosed herein to a cell. In an aspect, the cell can be a diploid cell with an engineered monoploid targeting locus. In an aspect, the cell can be a heteroallelic cells. In an aspect, the at least one strand of the double-stranded nucleic acid constructs can comprise a selectable marker. In an aspect, the first and second strands of the double-stranded nucleic acid constructs disclosed herein can comprise a barcode sequence. In an aspect, the barcode sequence of each strand can be complementary to the barcode sequence of the other strand.

In some aspects, the method can further include selecting cells comprising the double-stranded nucleic acid construct based on the presence of the selectable marker. In an aspect, the cells can be selected by flow sorting or using antibiotic resistance or based on a chrompohore.

In an aspect, the method can also include exposing (or contacting) the cells to a test compound or test conditions. In an aspect, the test conditions can include pH or other environmental conditions known to one of ordinary skill in the art.

In some aspects, the method can further include selecting or sorting cells based on a physical or chemical property test condition. In an aspect, the cells can be selected by flow sorting.

In some aspects, the method can further include analyzing an effect of the test compound or test conditions. In some aspects, the effect of the test compound or test conditions can be performed by assaying the effect of the expression of the one or more reporter elements. The method as disclosed herein can also include isolating mRNA from the selected cells and reverse transcribing at least a portion of the mRNA from the GADE and/or GARE sequences to generate GADE and/or GARE cDNA. In an aspect, the GADE and/or GARE cDNA can be generated by harvesting the isolated cells, isolating mRNA and reverse transcribing at least a portion of the RNA to generate GADE and GARE cDNA sequences. In some aspects, the GADE and GARE sequences generated can be genomic DNA, RNA, ChiP-sequencing. Bioinformatic methods can be used to generate GADE and GARE sequences. In some aspects, the method further comprises analyzing the GADE and/or GARE cDNAs. In some aspects, the method disclosed herein includes identifying the barcodes of the GADE and GARE sequences. The barcode sequences can be identified using real-time PCR or NGS. Any method can be used to align the barcode sequences to assemble an output.

The GigaAssay described herein can be used to study any organism including but not limited to an animal, plant or a single-celled life form (e.g., bacterium). The organism can be a prokaryote or a eukaryote. The GigaAssay described herein can also be used to study viruses.

The GigaAssay, vectors and constructs described herein can be used to improve or study the function of any component of the vectors or constructs disclosed herein. For example, the GigaAssay, vectors and constructs described herein can be used to study or understand the effect of a driver element, a reporter element, a library of driver elements, a library of reporter elements, a promoter operably linked to a driver element or driver element library, a promoter operably linked to a reporter element or reporter element library, a GADEL, a GAREL, a library of promoters operably linked to a driver element or driver element library, a library of promoters operably linked to a reporter element or reporter element library, or a selectable marker.

In some aspects, exogenous conditions can be applied to a cell comprising a double-stranded nucleic acid construct as disclosed herein in order to determine the effect of the exogenous condition on a driver element, a reporter element, a library of driver elements, a library of reporter elements, a promoter operably linked to a driver element or driver element library, a promoter operably linked to a reporter element or reporter element library, a GADEL, a GAREL, a library of promoters operably linked to a driver element or driver element library, a library of promoters operably linked to a reporter element or reporter element library, or a selectable marker. Exogenous conditions can include any environmental factor (e.g. pH, heat, light, cellular stress), a potential therapeutic agent (e.g. an antibody, small molecule, therapeutic peptide), or any other agent that may affect one or more of the components of the disclosed vectors or constructs.

In some aspects, the endogenous environment of a cell comprising a double-stranded nucleic acid construct as disclosed herein can be analyzed in order to determine the effect of the endogenous environment of the cell on a driver element, a reporter element, a library of driver elements, a library of reporter elements, a promoter operably linked to a driver element or driver element library, a promoter operably linked to a reporter element or reporter element library, a GADEL, a GAREL, a library of promoters operably linked to a driver element or driver element library, a library of promoters operably linked to a reporter element or reporter element library, or a selectable marker. Exogenous conditions can include any environmental factor (e.g. pH, heat, light, cellular stress), a potential therapeutic agent (e.g. an antibody, small molecule, therapeutic peptide), or any other agent that may affect one or more of the components of the disclosed vectors or constructs.

As provided herein, in an aspect, the GigaAssay can be used recursively.

EXAMPLES

Example 1. HIV Tat Transcription Factor Mutants Activate a GFP Reporter

The GigaAssay system was tested with HIV Tat activity because it has important clinical significance concerning HIV latency and because it is a well-studied protein (Das et al., 2011; Donahue et al., 2012), thus a rich source of benchmark data. There have been 33 previous mutagenesis reports examining how 316 different Tat site directed and truncation mutants differentially affect Tat-driven transcription; there are 1827 possible mutants in this 87 amino acid protein. These experiments were performed with several different types of assays and conditions, so thus, there are several ambiguities among published results. The GigaAssay analysis of Tat will standardize the analysis of the mutants, resolve ambiguities, and complete any missing data.

Figure 3:
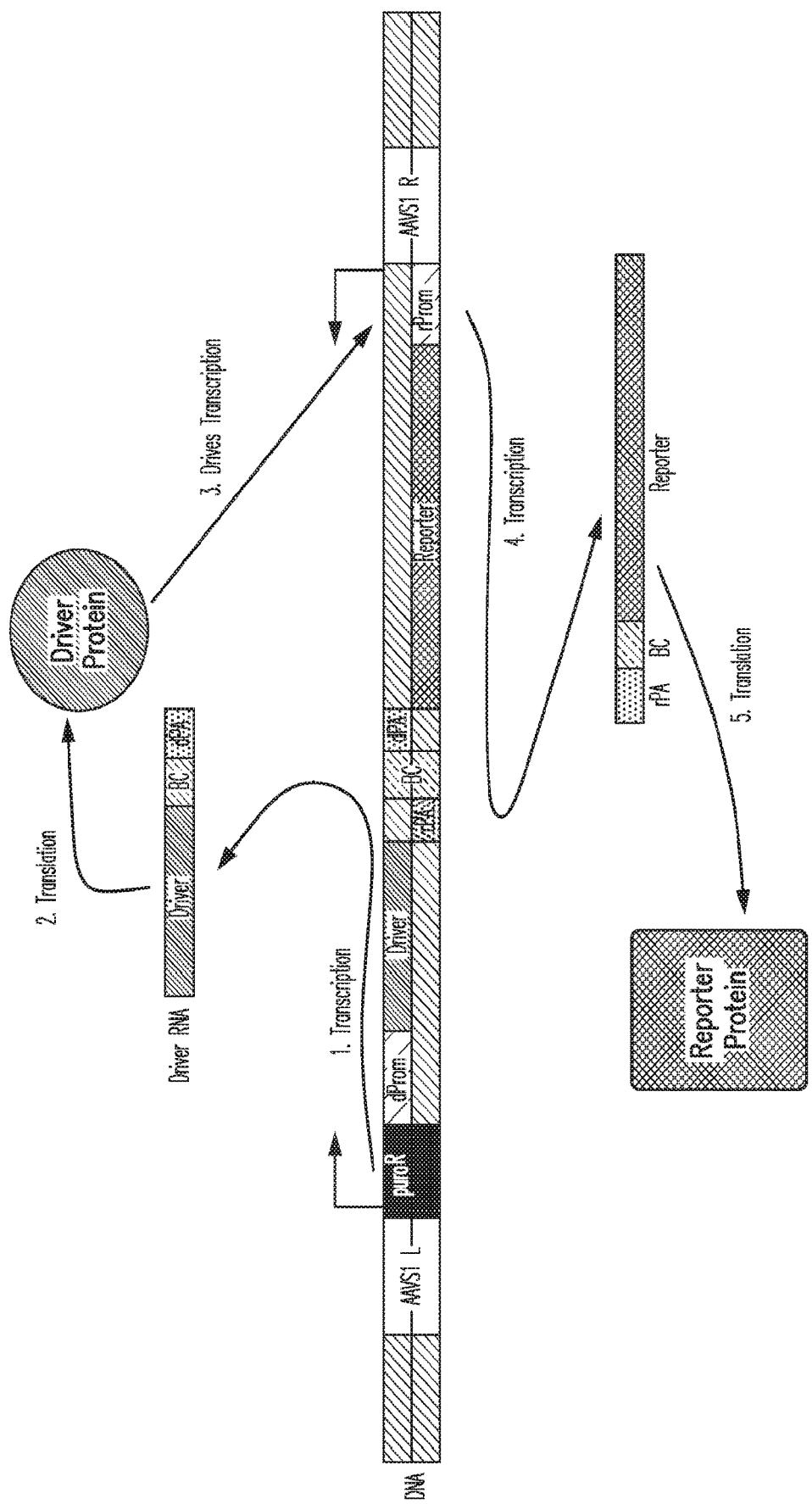
FIG. 3 shows the generation of a readout from a vector described herein.

For the validation experiments, HIV Tat was selected as the GADE and its activity was by its ability to transactivate the HIV long terminal repeat (LTR) to express the GFP (GARE; FIG. 3). The activity of the mutant Tat to drive the GFP transcript from the same plasmid template can be tracked using the barcode sequence. The mutant tat can be sequenced by NGS and its reporter GFP transcripts readout can be measured either by NGS (cluster readout) and/or flow cytometry. The GigaAssay cassette plasmid was constructed with wild type or two different Tat mutants as the GADE. LTR-GFP on the opposing strand was the GARE in the GigaAssay Cassette construct. To measure the output of the GARE, GFP expression was analyzed by both fluorescence microscopy and GFP mRNA levels were measured by real time PCR.

FIG. 3 shows the following. Tat can be the transactivator protein (GADE) from HIV that can transactivate the LTR promoter to drive the expression of its downstream gene, for example, GFP (GARE). The Giga assay cassette can also have a coding sequence for both the Tat and the GFP gene. The Tat gene represented by its mutant forms in the GigaAssay plasmid construct can affect the expression of GFP and can be interpreted as gain or loss of Tat protein function.

Figure 4B:
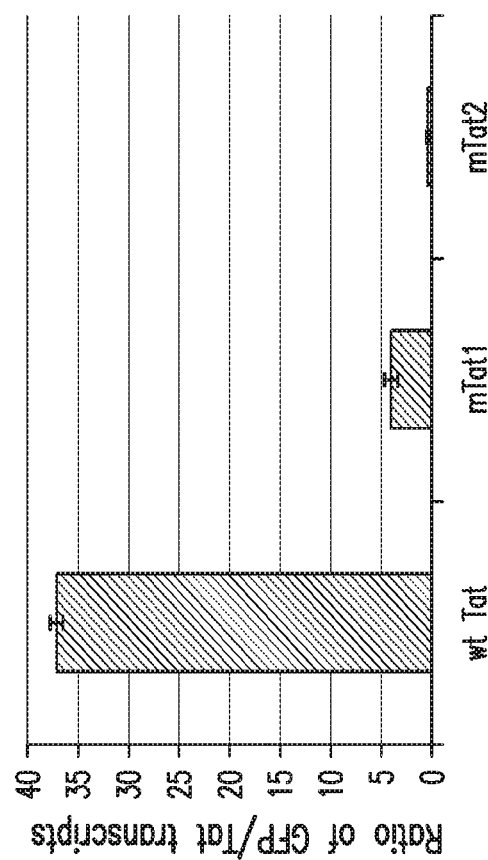
FIGS. 4A-B shows the results of a method of using a vector comprising a double-stranded nucleic acid construct comprising a Tat driver element and a GFP reporter element.
Figure 4A:
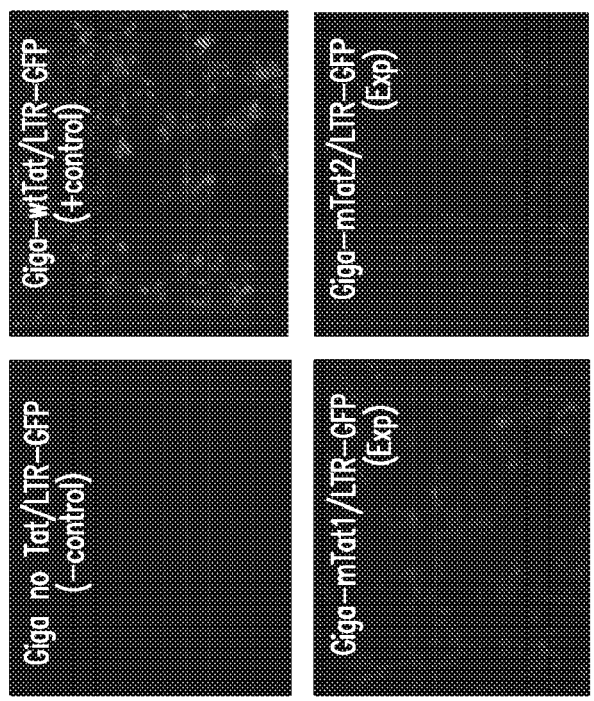

The wild type and mutant Tat GigaAssay cassette plasmid constructs were each transiently transfected into hEKLentiX293T cells. Forty-eight hours post-transfection, the cells were analyzed by florescence microscopy for Tat-driven GFP fluorescence. The cells transfected with wild type Tat showed relatively more GFP fluorescence than the two Tat mutants (FIG. 4A). The cells were harvested, RNA isolated, and reverse transcribed to cDNA. cDNAs from wild type Tat, and two mutant Tats were pooled together such that the barcode sequence can distinguish the transcripts. Primers were designed using barcode sequence information and used for performing real time PCR to measure the Tat and GFP transcripts. The specific barcodes in the wild type and mutant Tat and GFP transcripts were amplified using primers and the respective transcripts were analyzed. Standard deviations are calculated from 3 independent experiments (n=3). The two Tat mutants (E2G, D5G, E9G (mTat1) and C27S (mTat2)) exhibited markedly reduced transactivation of GFP transcription when compared to wild type Tat and were at levels similar to that previously published (FIG. 4B)(Ulich et al.). This experiment demonstrates the feasibility of this system, which can be scaled to analyze millions of mutant forms of GADEs and/or GAREs.

Figure 5:
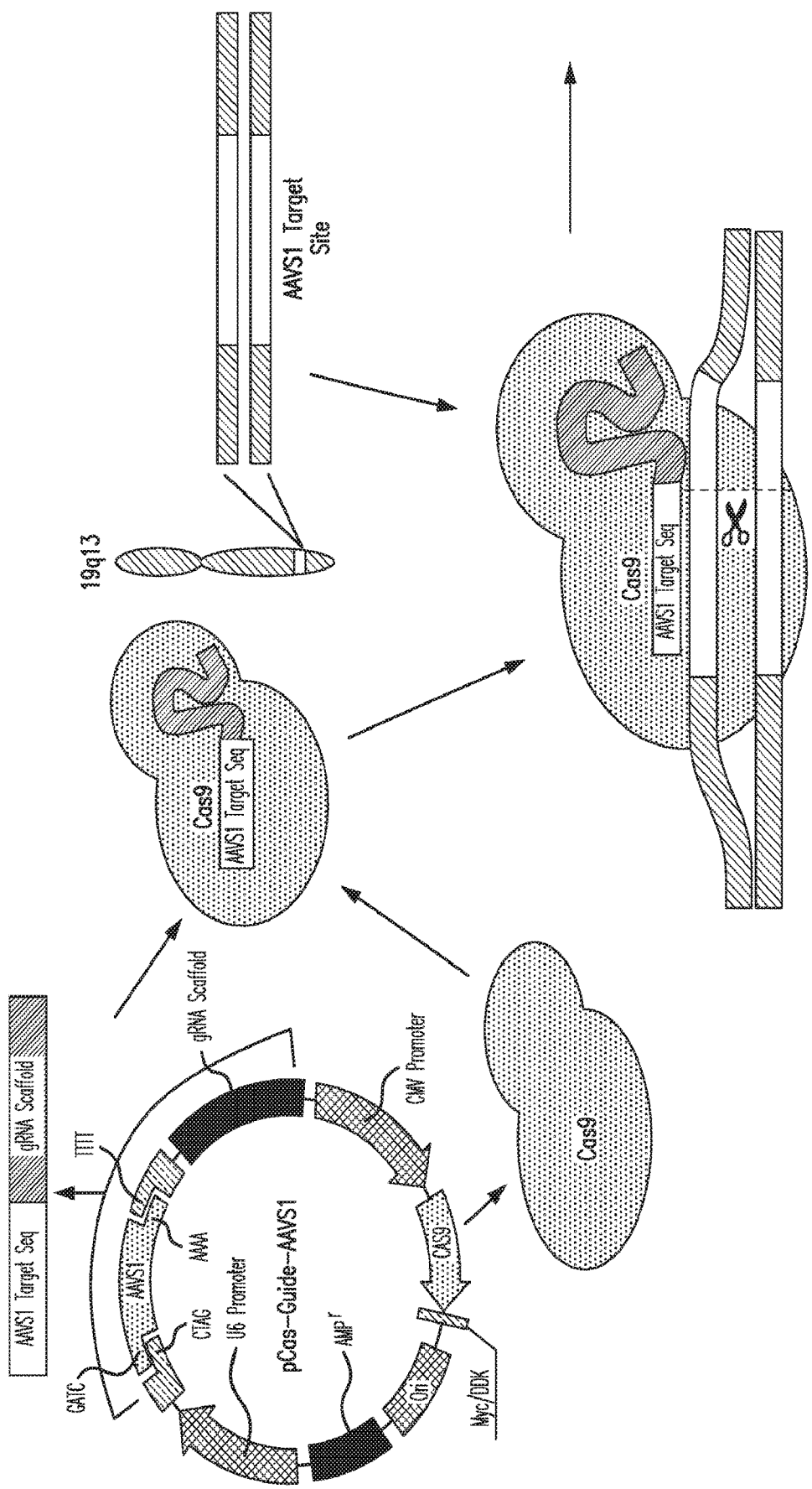
FIG. 5 shows an example of the generation of a cell line that has a heteroallelic AAVS1 locus.
Figure 5:
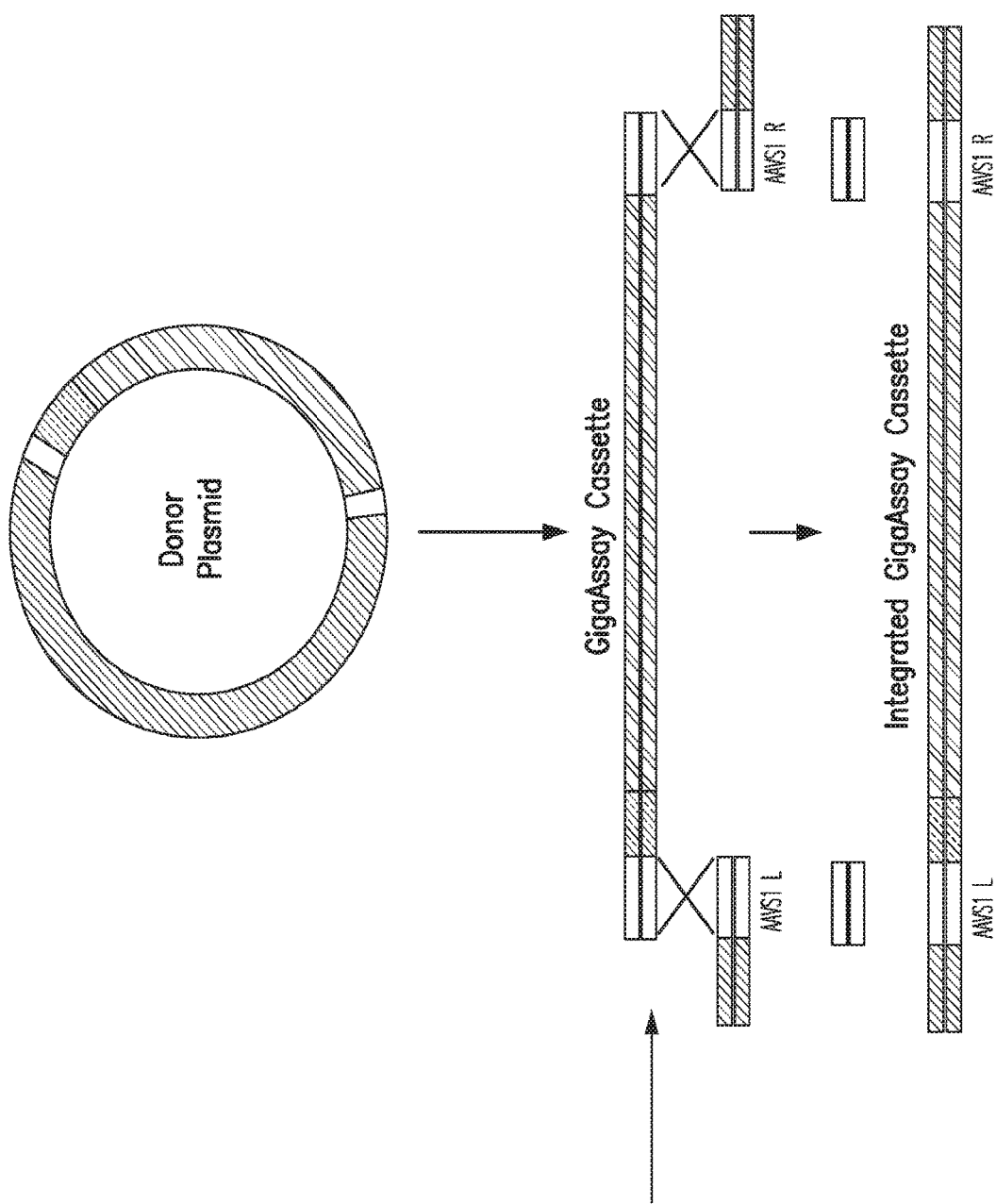

The GigaAssay cassette vector can be designed for specific integration of a single vector into a mammalian cell. Thus, stable transfection of a GigaAssay plasmid library will produce a large cell population where small clonal cell groups will each have a different clone from the library. When a library of mutant GADEs with a GARE is co-transfected into cells along with pCas-Guide-AAVS1 (Origene GE100023), a double-strand break can be introduced at the AAVS1 site by the Cas-9 using the gRNA (FIG. 5) and the GigaAssay cassette can be integrated by homologous recombination at the same AAVS1 site in each cell. The recombinant cells with stably integrated vectors can be selected with a selectable marker. More specifically, FIG. 5 shows that the pCas-Guide-AAVS1 (Origene GE100023) expresses U6 promoter driven gRNA that targets human AAVS1 site and CMV promoter driven Cas-9. Cas-9 is guided by the gRNA to the human AAVS1 site where it introduces a double-stranded break. The donor plasmid having the GigaAssay cassette flanked on either side by left and right homologous AAVS1 sequence allows the introduction of GigaAssay cassette at the human AAVS1 site by homologous recombination.

Example 2. HEK-293 Cell Line Heteroallelic for the AAVS Locus

To achieve stable integration of a single GigaAssay cassette at a specific site in each cell, a heteroallelic site where one allele accepts integration was required. The AAVS1 safe harbor locus was targeted such that when one allele contained an insertion, the AAVS1 arms facilitate insertion of the GigaAssay cassette into the wild type AAVS1 locus and not the one containing the insertion (FIG. 5).

Figure 6:
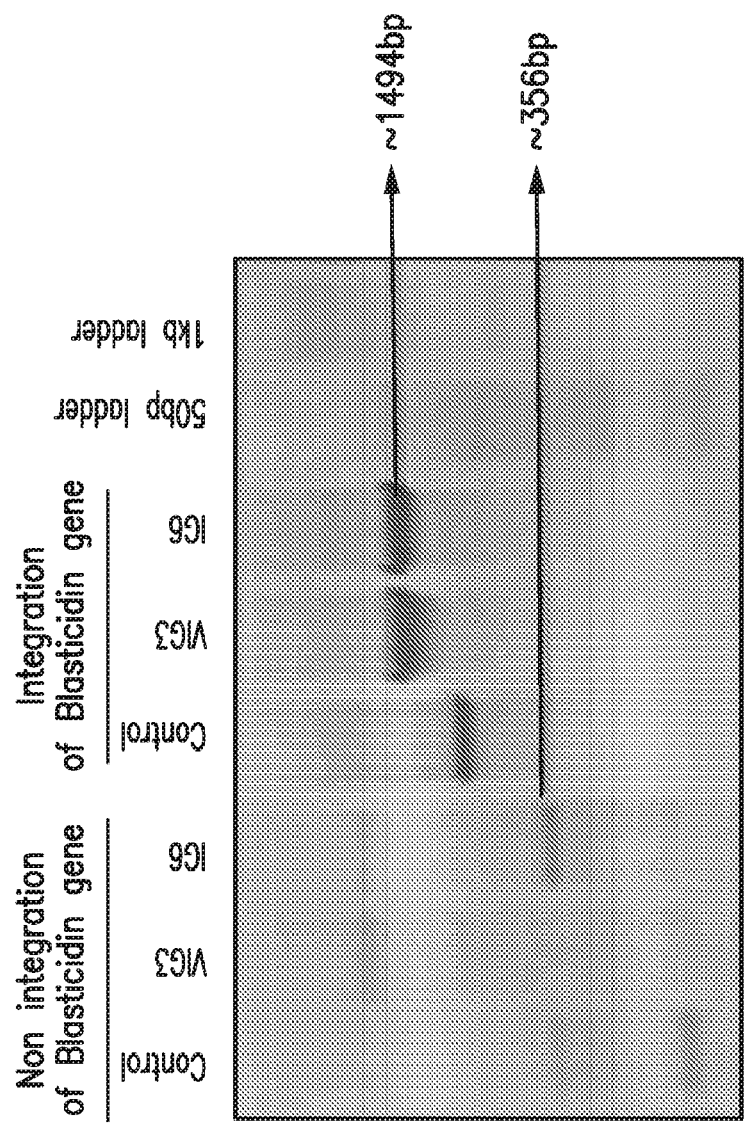
FIG. 6 shows the screening for a hEK-LentiX293T cell line with a heteroallelic AAVS1 locus.

Genomic DNA was cleaved by transfection with a pCas-Guide-AAVS1 plasmid expressing CRISPR/Cas9 and a gRNA targeting a segment of the AAVS1 locus on 19q13 (FIG. 5). This plasmid was co-transfected with a donor plasmid for insertion and poison-based selection for integrated cells. After selection and subcloning, clonal lines with one damaged allele (heteroallelic) were identified by PCR screening (FIG. 6).

Specifically, 10 million hEKLentiX293T cells were co-transfected with 2.5 µg of pCas-Guide-AAVS1 (Origene GE100023) and 2.5 µg pBSK-Blasticidin-AAVS1. The pBSK-Blasticidin-AAVS1 has flanking AAVS1 homology arms on either side of the Blasticidin gene for targeted integration. pCas-Guide-AAVS1 induced a double-stranded break at AAVS1 site for subsequent integration of the blasticidin resistance gene.

Clonal selection of cell lines resistant to Blasticidin were further screened by PCR for a cell line with a heteroallelic insertion with integration of Blasticidin gene in one AAVS1 allelic site but not on the other AAVS1 allelic site. As shown in FIG. 6, the control has no blasticidin integration, whereas the IG6 clone has homoallelic blasticidin integration, and the VIG3 clone has the desired homoetero allelicblasticidin integration. The VI G3 clone is named hEK-293T/AAVS1 (−/+). The presence of one AAVS1 site permits stable integration of one GigaAssay Cassette/cell. These cells can be used for many other types of GigaAssays.

For the screening for a hEK-lenitX293T cell line with a heteroallelic AAVS1 locus, agarose gel electrophoresis analysis for the detection of integration of Blasticidin gene at the AAVS1 site was carried out. As shown in FIG. 6, control cells do not have integration of Blasticidin gene at the AAVs1 site while IG6 shows amplification for Blasticidin integration, and therefore, is Homoallelic. VIG3 shows amplification for both integration of Blasticidin gene at the AAVS1 site and also amplification for non-integration indicating that is Heteroallelic cell line for AAVS1 site.

Example 3. Library Design and Construction

Figure 7A:
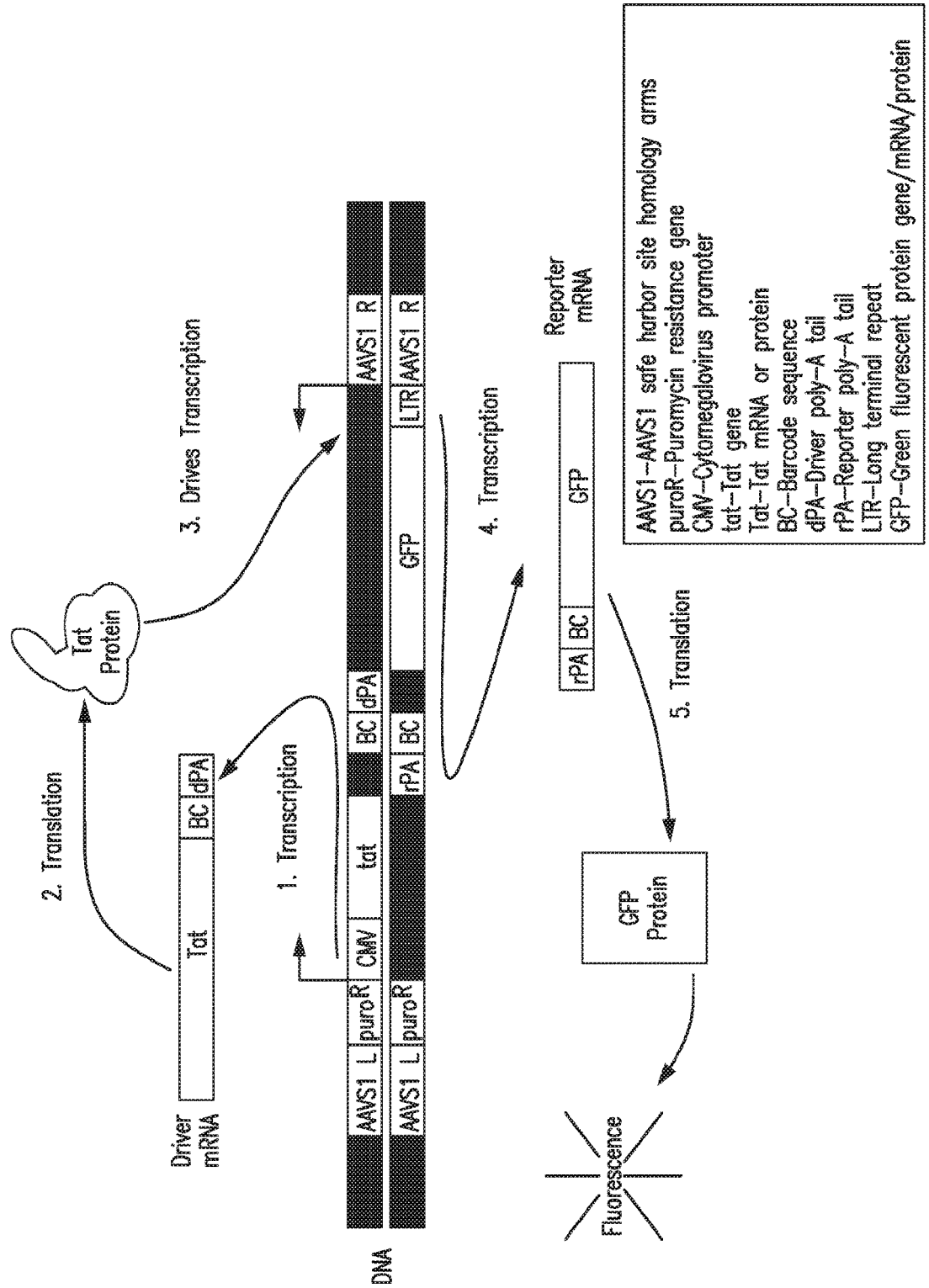
FIGS. 7A-B shows an exemplary method of using a vector comprising double-stranded nucleic acid construct comprising a Tat gene and a GFP reporter element and the design thereof.
Figure 7B:
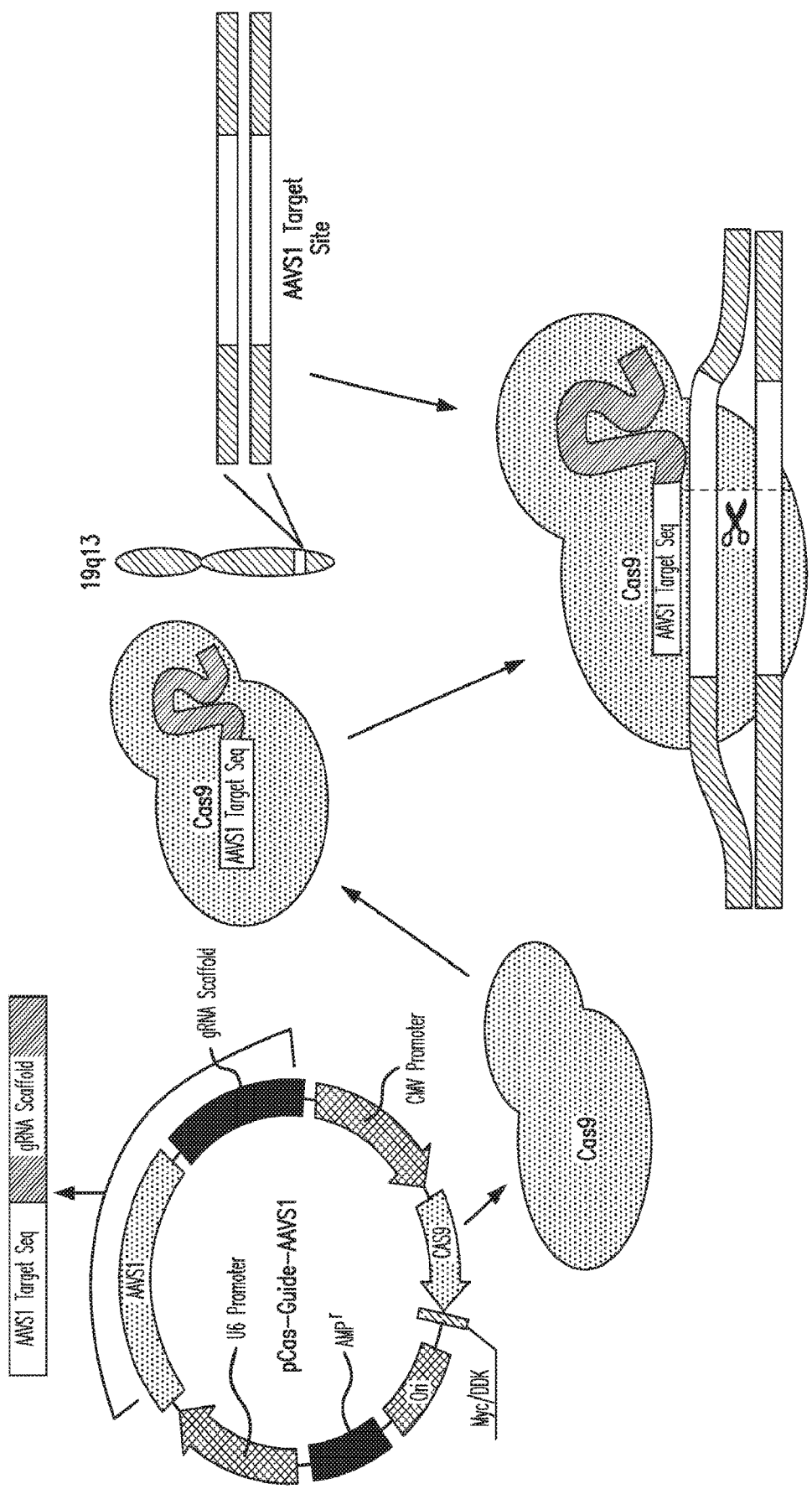
Figure 7B:
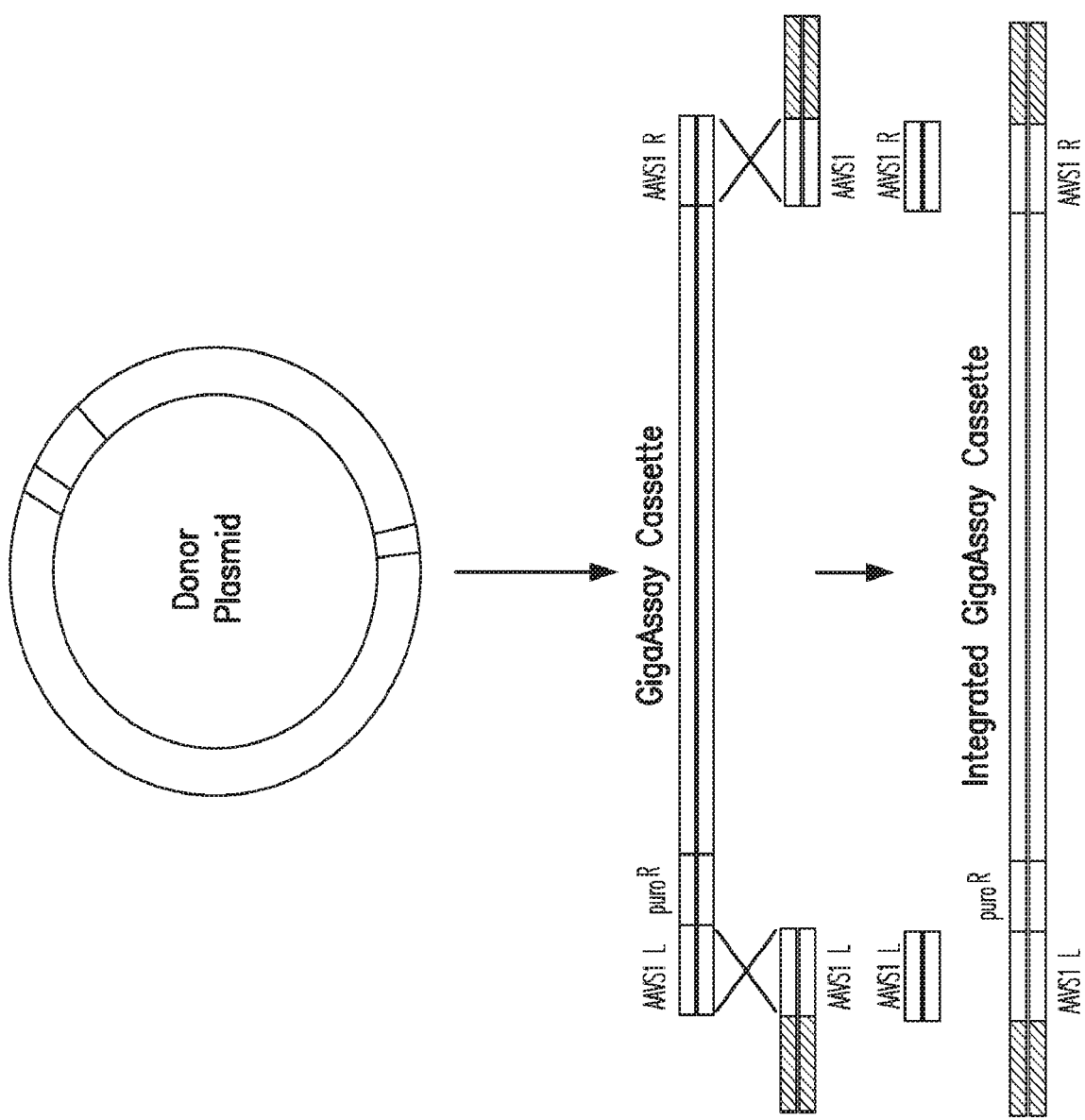

The randomly mutated Tat (rm-Tat)—HIV LTR-GFP GigaAssay cassette is shown in FIG. 7. A library of rm-Tat clones was created by error-prone PCR using Genemorph® II Random Mutagenesis kit(Agilent). rm-Tat PCR reactions were purified with the Clonetech gel extraction kit. For library cloning, the purified rm-Tat PCR products and the GigaAssayCassette vector were sequentially digested with restriction endonucleases KpnI and EcoRI, and desired fragments were purified. The (GigaAssay cassette vector) and insert (rm-Tat; 1:4 ratio) were ligated for 30 min at 25° C. with electroligase (New England Biolabs). The ligase was inactivated at 65° C. for 15 min, DNA was ethanol precipitated and drop-dialyzed using a membrane filter (MF-Millipore) for 2 hr. The drop-dialyzed ligated library was transformed into 10G ELITE elecetrocompetent cells (Lucigen) by electroporation to generate rm-Tat GigaAssay cassette plasmid library. The transformation efficiency was ~5 million transformants/µg (~2 million total clones). All colonies were scrapped from the LB-ampillicin plates and plasmids were isolated using plasmid midiprep kit (Invitrogen).

Next, the library was barcoded. To generate random double-stranded barcodes for insertion, 32 single-stranded random oligomers were commercially synthesized (Genelink). Complementary strands were synthesized by PCR in a single cycle reaction with stochiometric concentrations of primer. The resulting double-stranded barcodes were designed with AscI and AsiSI restriction endonuclease sites flanking each end for cloning into the rm-Tat GigaAssay cassette plasmid library.

The rm-Tat-GigaAssay cassette plasmid library and the double-stranded barcodes were digested with AscI and AsiSI and ligated with electroligase (NEB). The molar ratio of vector to insert was 1:6. The resulting barcoded library was drop-dialyzed and transformed into 10G ELITE electrocompetent cells (Lucigen) by electroporation. to generate rm-Tat Giga plasmid-BC library. The colonies from the rm-Tat-GigaAssay cassette barcoded (rm-Tat/LTR-GFP/BC) library were scrapped from the LB-ampicillin plates and plasmids were isolated with a midiprep kit (Invitrogen). Approximately 2 million transformants/µg of library or 1.4 million total transformants were obtained.

FIGS. 7 and 9 show the following. In FIGS. 7A and 9A, the flanking arms (e.g., 3' ARM and 5' ARM) help with the integration of the GigaAssay cassette at the AAVS1 site. puroR is the puromycin resistance gene and helps in the selection of the human cells with the integrated GigaAssay cassette. CMV is the CMV promoter which drives the expression of Tat gene. Right PA is the SV40 transcription terminator of the Tat transcript and carries the signal for addition of Poly(A) tails. LTR is the promoter that drives the expression of GFP protein. Left PA is the synthetic transcription terminator that has the Poly(A) signal for the GFP transcripts. The sequence for LTR, GFP and left PA is read from bottom strand of DNA and therefore the sequence is read from the opposite direction. Left PA will not code for a Poly(A) signal for Tat transcripts. Similarly right PA will not code for a Poly(A) signal for GFP transcripts. BS is the barcode sequence or specific 32-mers that is expressed as 3' non-coding RNA of the Tat and GFP transcripts. The barcode sequence of the Tat transcripts is complementary to the barcode sequence of the GFP transcript as Tat transcripts are coded by the top strand and GFP transcripts from the bottom strand of the DNA. FIGS. 7B and 9B show the double-strand break mediated by gRNA-Cas-9 at AAVS1 site and permits the GigaAssay cassette to integrate at the human AAVS1 site by homologus recombination.

Example 4. GigaAssay of the Rm-Tat/LTR Reporter Library

Approximately 50 of the rm-Tat/LTR-GFP/Bc library was transfected into 35 million hEK-293T/AAVS1(−/+) cells using lipofectomine (Invitrogen). The SCR7 ligase inhibitor (0.1 µM) was added 6 hours post-transfection to enhance homologous recombination (Chu et al., 2015). After 48 hours cultured in the presence of 1 µg/ml puromycin for 21 days, cells were harvested by trypinization, and flow sorted into 3 different populations based upon levels of GFP fluorescence (no-GFP, low-GFP and high-GFP). The RNA from each cellular pool was isolated and reverse transcribed into cDNA. The GFP and Tat transcripts were sequenced by RNASeq with paired-end reads on an Illumina MiSeq. RNASeq libraries for each flow sorted pool were barcoded separately to identify GFP fluorescence levels. Results were analyzed with Base Space, Illumina and custom GigaAssay software to determine the identity of the Tat mutant and expression levels of the Tat mutant and GFP. The GigaAssay permitted analysis of the transcriptional activity of millions of Tat mutants.

Example 5. Processing and Preparation of Samples for NGS

The cells are selected under puromycin (1 µg/ml) for a period ranging from 3-5 weeks and then harvested for DNA and RNA extraction. RNA isolated from cells depending on the requirement, can be incubated with oligodT beads and rRNA depletion for mRNA enrichment. Next, RNA is reverse transcribed to cDNA using oligodT/random primers/ gene specific primers of GADE and GARE. Second strand cDNA synthesis will be performed using second strand marking kit. The cDNA double stranded which is then end repaired before performing adaptor ligation. After adaptor ligation, the cDNA is PCR enriched. The samples are treated with Agencourt Ampure XP beads or any similar kit wherever applicable to ensure the purity by removal of salts, dNTP, primers, oligodT.

REFERENCES

Aloisio, M., Licastro, D., Caenazzo, L., Torboli, V., D'eustacchio, A., Severini, G. M., and Athanasakis, E. (2016). A technical application of quantitative next generation sequencing for chimerism evaluation. Mol. Med. Rep. 14, 2967-2974.

Balla, S., Thapar, V., Verma, S., Luong, T., Faghri, T., Huang, C.-H., Rajasekaran, S., del Campo, J. J., Shinn, J. H., Mohler, W. A., et al. (2006). Minimotif Miner: a tool for investigating protein function. Nat. Methods 3, 175-177.

Chu, V. T., Weber, T., Wefers, B., Wurst, W., Sander, S., Rajewsky, K., and Kühn, R. (2015). Increasing the efficiency of homology-directed repair for CRISPR-Cas9-induced precise gene editing in mammalian cells. Nat. Biotechnol. 33, 543-548.

Das, A. T., Harwig, A., and Berkhout, B. (2011). The HIV-1 Tat Protein Has a Versatile Role in Activating Viral Transcription ∇. J. Virol. 85, 9506-9516.

Donahue, D. A., Kuhl, B. D., Sloan, R. D., and Wainberg, M. A. (2012). The Viral Protein Tat Can Inhibit the Establishment of HIV-1 Latency. J. Virol. 86, 3253-3263.

Green, C. B., Zhao, X., Yeater, K. M., and Hoyer, L. L. (2005). Construction and real-time RT-PCR validation of *Candida albicans* PALS-GFP reporter strains and their use in flow cytometry analysis of ALS gene expression in budding and filamenting cells. Microbiol. Read. Engl. 151, 1051-1060.

Gurtu, V., Yan, G., and Zhang, G. (1996). IRES bicistronic expression vectors for efficient creation of stable mammalian cell lines. Biochem. Biophys. Res. Commun. 229, 295-298.

Jiang, T., Xing, B., and Rao, J. (2008). Recent developments of biological reporter technology for detecting gene expression. Biotechnol. Genet. Eng. Rev. 25, 41-75.

Kain, S. R., Adams, M., Kondepudi, A., Yang, T. T., Ward, W. W., and Kitts, P. (1995). Green fluorescent protein as a reporter of gene expression and protein localization. BioTechniques 19, 650-655.

Mann, M. J., and Dzau, V. J. (2000). Therapeutic applications of transcription factor decoy oligonucleotides. J. Clin. Invest. 106, 1071-1075.

Pearson, W. R. (1990). Rapid and sensitive sequence comparison with FASTP and FASTA. Methods Enzymol. 183, 63-98.

Puntervoll, P., Linding, R., Gemünd, C., Chabanis-Davidson, S., Mattingsdal, M., Cameron, S., Martin, D. M. A., Ausiello, G., Brannetti, B., Costantini, A., et al. (2003). ELM server: A new resource for investigating short functional sites in modular eukaryotic proteins. Nucleic Acids Res. 31, 3625-3630.

Ujihira, T., Ikeda, K., Suzuki, T., Yamaga, R., Sato, W., Horie-Inoue, K., Shigekawa, T., Osaki, A., Saeki, T., Okamoto, K., et al. (2015). MicroRNA-574-3p, identified by microRNA library-based functional screening, modulates tamoxifen response in breast cancer. Sci. Rep. 5.

Vyas, J., Nowling, R. J., Maciejewski, M. W., Rajasekaran, S., Gryk, M. R., and Schiller, M. R. (2009). A proposed syntax for Minimotif Semantics, version 1. BMC Genomics 10, 360.

What is claimed is:

1. A vector comprising a double-stranded nucleic acid construct, wherein the double-stranded nucleic acid construct comprises a first strand and a second strand, wherein the first strand comprises from 5' to 3', a left arm of a AAVS1 locus sequence;

a nucleic acid sequence encoding puromycin N-acetyl-transferase; a CMV promoter; a tat cDNA coding sequence; a 3' UTR, wherein the 3' UTR comprises a nucleic acid sequence complementary to a synthetic poly(A) signal of the 3'UTR of the second strand, a first barcode sequence complementary to a second barcode sequence of the second strand, and a polySV40(A) sequence; a nucleic acid sequence complementary to a GFP coding sequence of the second strand, a sequence complementary to a LTR promoter of the second strand; a sequence complementary to the right arm of the AAVS1 locus sequence of the second strand; and a functional sequence;

wherein the second strand comprises from 5' to 3', a right arm of a AAVS1 locus sequence; a LTR promoter; a GFP coding sequence; a 3' UTR, wherein the 3'UTR comprises a nucleic acid sequence complementary to the polySV40(A) sequence of the 3' UTR of the first strand, the second barcode sequence complementary to the first barcode sequence of the first strand, and a synthetic poly(A) signal; a nucleic acid sequence complementary to the tat cDNA coding sequence and the CMV promoter of the first strand; a nucleic acid sequence encoding puromycin N-acetyl-transferase; a nucleic acid sequence complementary to the left arm of the AAVS1 locus sequence of the first strand; and a functional sequence.

* * * * *